US010253102B2

(12) United States Patent
Gromada et al.

(10) Patent No.: US 10,253,102 B2
(45) **Date of Patent: *Apr. 9, 2019**

(54) ANTIGEN-BINDING PROTEINS THAT ACTIVATE THE LEPTIN RECEPTOR

(71) Applicant: Regeneron Pharmaceuticals, Inc., Tarrytown, NY (US)

(72) Inventors: Jesper Gromada, Scarsdale, NY (US); Panayiotis Stevis, West Orange, NJ (US); Judith Altarejos, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,848

(22) Filed: Jun. 13, 2018

(65) Prior Publication Data

US 2018/0282421 A1 Oct. 4, 2018

Related U.S. Application Data

(63) Continuation of application No. 15/290,967, filed on Oct. 11, 2016, now Pat. No. 10,023,644.

(60) Provisional application No. 62/240,021, filed on Oct. 12, 2015, provisional application No. 62/359,757, filed on Jul. 8, 2016, provisional application No. 62/375,495, filed on Aug. 16, 2016, provisional application No. 62/393,143, filed on Sep. 12, 2016.

(51) Int. Cl.

| | |
|---|---|
| ***C07K 16/00*** | (2006.01) |
| ***C12P 21/08*** | (2006.01) |
| ***C07K 16/28*** | (2006.01) |
| ***A61K 39/395*** | (2006.01) |
| *A61K 39/00* | (2006.01) |

(52) U.S. Cl.

CPC ........ *C07K 16/2869* (2013.01); *A61K 39/395* (2013.01); *A61K 2039/505* (2013.01); *C07K 2317/21* (2013.01); *C07K 2317/33* (2013.01); *C07K 2317/34* (2013.01); *C07K 2317/565* (2013.01); *C07K 2317/75* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 6,005,080 | A | 12/1999 | Snodgrass et al. | |
| 6,380,363 | B1 | 4/2002 | Tartaglia et al. | |
| 6,977,240 | B1 * | 12/2005 | Tartaglia .............. | C07K 14/715 424/131.1 |
| 7,524,937 | B2 | 4/2009 | Carter et al. | |
| 7,575,878 | B2 | 8/2009 | Tavernier et al. | |
| 7,863,240 | B2 | 1/2011 | Ilan et al. | |
| 8,697,396 | B2 | 4/2014 | Dall'Acqua et al. | |
| 8,969,291 | B2 | 3/2015 | Ilan et al. | |
| 10,023,644 | B2 | 7/2018 | Gromada et al. | |
| 2014/0134162 | A1 | 5/2014 | Stavenhagen et al. | |
| 2014/0171623 | A1 | 6/2014 | Dall'Acqua et al. | |
| 2014/0243504 | A1 | 8/2014 | Davis et al. | |
| 2018/0037648 | A1 | 2/2018 | Ilan et al. | |
| 2019/0002569 | A1 | 1/2019 | Belaid-Choucair et al. | |

FOREIGN PATENT DOCUMENTS

| | | | |
|---|---|---|---|
| AU | 2004201496 | C1 | 8/2018 |
| EP | 981365 | B1 | 12/2004 |
| EP | 885299 | B1 | 10/2005 |
| EP | 0730606 | B1 | 11/2005 |
| EP | 1619250 | B1 | 11/2009 |
| EP | 1019432 | B1 | 1/2012 |
| WO | 1996/08510 | | 3/1996 |
| WO | 1997/019952 | | 6/1997 |
| WO | 1997/025425 | | 7/1997 |
| WO | 1997/26272 | | 7/1997 |
| WO | 1997/26370 | | 7/1997 |
| WO | 1997/26523 | | 7/1997 |
| WO | 1997/27286 | | 7/1997 |
| WO | 1997/41263 | | 11/1997 |
| WO | 1998/48831 | | 11/1998 |
| WO | 2006/053883 | | 5/2006 |
| WO | 2014/043361 | A1 | 3/2014 |
| WO | 2015/124588 | | 8/2015 |
| WO | 2017/066204 | A1 | 4/2017 |

OTHER PUBLICATIONS

Accession No. NP_002294.2.
Accession No. XP_005543194.1.
Ahmann, et al. (2015) "Efficacy and safety of liraglutide versus placebo added to basal insulin analogues (with or without metformin) in patients with type 2 diabetes: a randomized, placebo-controlled trial," Diabetes, Obesity and Metabolism 17(11):1056-1064.

(Continued)

*Primary Examiner* — Shulamith H Shafer

(74) *Attorney, Agent, or Firm* — FisherBroyles, LLP; Cara L Crowley-Weber; Thomas Triolo

(57) ABSTRACT

The present invention provides antibodies and antigen-binding fragments of antibodies that bind to leptin receptor (LEPR), and methods of using the same. According to certain embodiments, the invention includes antibodies and antigen-binding fragments of antibodies that bind LEPR and activate LEPR signaling. In other embodiments, the invention includes antibodies and antigen-binding fragments of antibodies that bind to LEPR and enhance sensitization of LEPR to an antigen. In certain embodiments, the invention includes antibodies and antigen-binding fragments of antibodies that bind LEPR in the presence and absence of leptin. In certain embodiments, the invention includes antibodies and antigen-binding fragments of antibodies that induce signaling in cells expressing LEPR mutants that otherwise exhibit defective or impaired signaling in the presence of leptin. The antibodies and antigen-binding fragments of the present invention are useful for the treatment of lipodystrophies and other diseases and disorders associated with or caused by leptin deficiency or leptin resistance.

29 Claims, 8 Drawing Sheets

Specification includes a Sequence Listing.

(56) References Cited

OTHER PUBLICATIONS

Al-Lazikani, et al. (1997) "Standard Conformations for the Canonical Structures of Immunoglobulins," J. Mol. Biol. 273:927-948.
Allison, et al. (2014) "Connecting leptin signaling to biological function," Journal of Endocrinology 223:T25-T35.
Altschul, et al. (1990) "Basic Local Alignment Search Tool," J. Mol. Biol. 215:403-410.
Altschul, et al. (1997) "Grapped BLAST and PSI-BLAST: a new generation of protein database search programs," Nucleic Acids Res. 25(17):3389-402.
Bhaskar, et al. (2016) "An Allosteric Antibody to the Leptin Receptor Reduces Body Weight and Reverses the Diabetic Phenotype in the Lepob/Lepob Mouse," Obesity 00:(00) 1-8.
Bray and Wadden (2015) "Improving Long-Term Weight Loss Maintenance: Can We Do It?," Obesity 23:2-3.
Carpenter, et al. (2012) "Structure of the Human Obesity Receptor Leptin-Binding Domain Reveals the Mechanism of Leptin Antagonism by a Monoclonal Antibody," Structure 20:487-497.
Deddish et al. (1990) "Carboxypeptidase M in Madin-Darby Canine Kidney Cells" J. Biological Chemistry 265 (25):15083-15089.
Ehring (1999) "Hydrogen Exchange / Electrospray Ionization Mass Spectrometry Studies of Structural Features of Proteins and Protein/Protein Interactions," Analytical Biochemistry 267(2):252-259.
Engen and Smith (2001) "The Basics of Ion Chromatography," Anal. Chem. 73:256A-265A.
Farooqi, et al. (2007) "Clinical and Molecular Genetic Spectrum of Congenital Deficiency of the Leptin Receptor," N. Engl. J. Med. 356:237-247.
Farooqui, et al. (2002) "Beneficial effects of leptin on obesity, T cell hyporesponsiveness, and neuroendocrine/metabolic dysfunction of human congenital leptin deficiency," The Journal of Clinical Investigation 110(8):1093-1103.
Fazeli, et al. (2006) "Identification of a monoclonal antibody against the leptin receptor that acts as an antagonist and blocks human monocyte and T cell activation," Journal of Immunological Methods 312:190-200.
Friedman, et al. (2014) "20 Years of Leptin: Leptin at 20: an overview," J. Endocrinol. 223(1):T1-8.
Gonnet, et al. (1992) "Exhaustive Matching of the Entire Protein Sequence Database," Science 256: 1443-1445.
Goodson J.M., "Dental Applications" in: Medical Applications of Controlled Release, vol. 2, Chapter 6, Langer R.S., et al., eds., CRC Press, 1984, pp. 115-138.
Haniu, et al. (1998) "Human Leptin Receptor, Determination of Disulfide Structure and N-Glycosylation Sites of the Extracellular Domain*" J. Biol. Chem. 273(44): 28691-69.
Iepsen, et al. (2014) "Treatment with a GLP-1 receptor agonist diminishes the decrease in free plasma leptin during maintenance of weight loss," International Journal of Obesity, 39(5):834-841.
Junghans, et al. (1990) "Anti-Tac-H, a Humanized Antibody to the Interleukin 2 Receptor with New Features for Immunotherapy in Malignant and Immune Disorders," Cancer Research 50:1495-1502.
Kazane, et al. (2013) "Self-Assembled Antibody Multimers through Peptide Nucleic Acid Conjugation," Journal of the American Chemical Society, 135(1):340-346.
Klein, et al. (2012) "Progress in overcoming the chain association issue in bispecific heterodimeric IgG antibodies," mAbs 4(6):653-663.
Kufer, et al. (2004) "A Revival of bispecific antibodies," Trends Biotechnolgy 22(5):238-244.
Langer (1990) "New Methods of Drug Delivery," Science 249:1527-1533.
Mancour, et al. (2012) "Ligand-Induced Architecture of the Leptin Receptor Signaling Complex," Molecular Cell 48:655-661.
Martin, et al. (1989) "Modeling antibody hypervariable loops: A combined algorithm," Proc. Natl. Acad. Sci. USA 86:9268-9272.
Mazen, et al. (2011) "Homozygosity for a novel missense mutation in the leptin receptor gene (P316T) in two Egyptian cousins with severe early onset obesity," Molecular Genetics and Metabolism 102:461-464.
Meehan, et al. (2016) "Metreleptin for injection to treat the complications of leptin eficiency in patients with congenital or acquired generalized lipodystrophy," Clinical Pharmacology 9(1):59-68.
Molek, et al. (2014) "Screening of synthetic phage display scFv libraries yields competitive ligands of human leptin receptor," Biochemical and Biophysical Research Communications, 452(3):479-483.
Mordenti, et al. (1991) "Interspecies Scaling of Clearance and Volume of Distribution Data for Five Therapeutic Protein," Pharmaceutical Research 8:1351-1359.
Paz-Filho, et al. (2014) "Leptin treatment: Facts and expectations," Metabolism, pp. 1-11, http://dx.doi.org/10.1016/j.metabol.2014.07.014.
PCT International Search Report and Written Opinion received for PCT/US2016/056465, dated Jan. 10, 2017.
Pearson (1994) "Using the FASTA Program to Search Protein and DNA Sequence Databases," Methods in Molecular Biology 24:307-331.
Peelman, et al. (2014) "Insights into signaling assemblies of the leptin receptor," Journal of Endocrinology 223:T9-T23.
Powell, et al. (1998) "Compendium of Excipients for Parenteral Formulations" PDA J. Pharm. Sci. Technol. 52:238-311.
Procaccini, et al. (2015) "Leptin in autoimmune diseases," Metabolism Clinical and Experimental 64:92-104.
Reddy, et al. (2000) "Elimination of Fc Receptor-Dependent Effector Functions of a Modified IgG4 Monoclonal Antibody to Human CD4," J. Immunol. 164:1925-1933.
Rosenbaum, et al. (2002) "Low Dose Leptin Administration Reverse Effects of Sustained Weight-Reduction on Energy Expenditure and Circulating Concentrations of Thyroid Hormones," The Journal of Clinical Endocrinology & Metabolism 87(5):2391-2394.
Rosenbaum, et al. (2005) "Low-dose leptin reverses skeletal muscle, autonomic, and neuroendocrine adaptations to maintenance of reduced weight" The Journal of Clinical Investigation 115(12):3579-3586.
Sefton (1987) "Implantable Pumps," CRC Critical Reviews in Biomedical Engineering 14(3):201.
Shimomura, et al. (1999) "Leptin reverses insulin resistance and diabetes mellitus in mice with congenital lipodystrophy," Nature 401:73-76.
Tartaglia (1997) "The Leptin Receptor*," J. Biol. Chem. 272(10):6093-6096.
Taylor, et al. (1992) "A transgenic mouse that express a diversity of human sequence heavy and light chain immunoglobulins," Nucleic Acids Research 20(23):6287-6295.
Hochleitner, et al. (2000) "Characterization of a discontinous epitope of the human immunodeficiency virus (HIV) core protein p24 by epitope excision and differential chemical modification followed by mass spectrometric peptide mapping analysis," Protein Science 9:487-496.
Tutt, et al. (1991) "Trispecific F(ab')3 Derivatives That use Cooperative Signaling Via the TCR/CD3 Complex and CD2 to Activate and Redirect Resting Cytotoxic T Cells," The Journal of Immunology 147(1):60-69.
Ussar, et al. (2011) "Receptor Antibodies as Novel Therapeutics for Diabetes," Science Translational Medicine, 3 (113):22-24.
Wu, et al. (1987) "Receptor-mediated in Vitro Gene Transformation by a Soluable DNA Carrier System," The Journal of Biological Chemistry 262(10):4429-4432.
Zabeau, et al. (2015) "Leptin: From structural insights to the design of antagonists," Life Sciences 140:49-56.
U.S. Appl. No. 16/222,800, filed Aug. 17, 2018, Gromada, et al.
Tartaglia et al., (1995) "Identification and Expression Cloning of a Leptin Receptor, OB-R", Cell, 83(7):1263-1271.

* cited by examiner

*P<0.05, Isotype Control vs H4H18482P2
@P<0.05, Isotype Control vs H4H18487P2
!P<0.05, Isotype Control vs H4H18492P2
#P<0.05, H4H18492P2 vs H4H18482P2
$P<0.05, H4H18492P2 vs H4H18487P2

ANTIGEN-BINDING PROTEINS THAT ACTIVATE THE LEPTIN RECEPTOR

This application is a continuation of U.S. patent application Ser. No. 15/290,967, filed Oct. 11, 2016, which claims the benefit of priority under 35 U.S.C. § 119(e) of U.S. Provisional Application Nos. 62/240,021, filed Oct. 12, 2015; 62/359,757, filed Jul. 8, 2016; 62/375,495, filed Aug. 16, 2016, and 62/393,143, filed Sep. 12, 2016, the disclosures of which are herein incorporated by reference in their entireties.

SEQUENCE LISTING

An official copy of the sequence listing is submitted concurrently with the specification electronically via EFS-Web as an ASCII formatted sequence listing with a file name of 10178US03_SEQ_LIST_ST25.TXT, a creation date of Jun. 13, 2018, and a size of about 105 kilobytes. The sequence listing contained in this ASCII formatted document is part of the specification and is herein incorporated by reference in its entirety.

FIELD OF INVENTION

The present invention is related to antibodies and antigen-binding fragments of antibodies that bind human leptin receptor (LEPR), and therapeutic and diagnostic methods of using those antibodies.

BACKGROUND

Leptin is a polypeptide hormone predominantly expressed by adipose tissue and is involved in the regulation of metabolism, energy balance and food intake. Leptin activity is mediated by interaction with, and signaling through, the leptin receptor. Leptin receptor, (also known as "LEPR," "WSX," "OB receptor," "OB-R," and "CD295") is a single-pass transmembrane receptor of the class I cytokine receptor family with a large (818 amino acid) extracellular domain. Leptin deficiency, leptin resistance, and certain LEPR signaling-defective/signaling impaired mutations, are associated with obesity, type 2 diabetes, dyslipidemia, lipodystrophies, hepatic steatosis, non-alcoholic and alcoholic fatty liver diseases, severe insulin resistance, Leprechaunism/Donohue syndrome, Rabson-Mendenhall syndrome, and related complications. Therapeutic approaches to address leptin resistance, leptin deficiency, and hypoleptinemia (e.g., lipodystrophy) have mostly focused on the delivery of supplemental leptin or leptin analogues to affected individuals. Such approaches, however, have generally shown limited efficacy, particularly in leptin-resistant individuals, and are frequently associated with adverse side effects. Thus, a need exists in the art for alternative approaches to treating leptin resistance and other conditions associated with leptin deficiency or hypoleptinemia.

BRIEF SUMMARY OF THE INVENTION

The present invention provides antibodies and antigen-binding fragments thereof that bind human leptin receptor (LEPR). The antibodies of the present invention are agonist antibodies; i.e., binding of the anti-LEPR antibodies of the invention to LEPR causes, inter alia, activation of leptin receptor signaling in cells. In certain embodiments, the antibodies of the present invention do not compete with leptin for binding to LEPR. The antibodies of the present invention are useful, e.g., for mimicking, substituting for, or supplementing the normal biological activity of leptin in a subject. The antibodies and antigen-binding fragments of the present invention are therefore useful in the therapeutic treatment of diseases and disorders associated with leptin resistance and leptin deficiency.

The antibodies of the invention can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., 2000, J. Immunol. 164:1925-1933).

Exemplary anti-LEPR antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-LEPR antibodies. Table 2 sets forth the nucleic acid sequence identifiers of the HCVRs, LCVRs, HCDR1, HCDR2 HCDR3, LCDR1, LCDR2 and LCDR3 of the exemplary anti-LEPR antibodies.

The present invention provides antibodies or antigen-binding fragments thereof that specifically bind LEPR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-LEPR antibodies listed in Table 1. In certain embodiments, the HCVR/LCVR amino acid sequence pair is selected from the group consisting of SEQ ID NOs: 2/10, 18/10, 26/10, 34/10, 42/10, 50/10, 58/66, 74/66 and 82/66.

The present invention also provides antibodies or antigen-binding fragments thereof that specifically bind LEPR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-LEPR antibodies listed in Table 1. In certain embodiments, the HCDR3/LCDR3 amino acid sequence pair is selected from the group consisting of SEQ ID NOs: 8/16, 24/16, 32/16, 40/16, 48/16, 56/16, 64/72, 80/72 and 88/72.

The present invention also provides antibodies or antigen-binding fragments thereof that specifically bind LEPR, comprising a set of six CDRs (i.e., HCDR1, HCDR2, HCDR3, LCDR1, LCDR2, and LCDR3) contained within any of the exemplary anti-LEPR antibodies listed in Table 1. In certain embodiments, the HCDR1, HCDR2, HCDR3, LCDR1, LCDR2, and LCDR3 amino acid sequences set is selected from the group consisting of SEQ ID NOs: 4, 6, 8, 12, 14, 16; 20, 22, 24, 12, 14, 16; 28, 30, 32, 12, 14, 16; 36, 38, 40, 12, 14, 16; 44, 46, 48, 12, 14, 16; 52, 54, 56, 12, 14, 16; 60, 62, 64, 68, 70, 72; 76, 78, 80, 68, 70, 72; and 84, 86, 88, 68, 70, 72.

In a related embodiment, the present invention provides antibodies, or antigen-binding fragments thereof that specifically bind LEPR, comprising a set of six CDRs (i.e., HCDR1, HCDR2, HCDR3, LCDR1, LCDR2, and LCDR3) contained within an HCVR/LCVR amino acid sequence pair as defined by any of the exemplary anti-LEPR antibodies listed in Table 1. For example, the present invention includes antibodies or antigen-binding fragments thereof that specifically bind LEPR, comprising the HCDR1, HCDR2, HCDR3, LCDR1, LCDR2, and LCDR3 amino acid sequences set contained within an HCVR/LCVR amino acid sequence pair selected from the group consisting of SEQ ID NOs: 2/10, 18/10, 26/10, 34/10, 42/10, 50/10, 58/66, 74/66 and 82/66. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-LEPR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-LEPR antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-LEPR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-LEPR antibody listed in Table 1.

The present invention also provides recombinant expression vectors capable of expressing a polypeptide comprising a heavy or light chain variable region of an anti-LEPR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a pharmaceutical composition comprising a recombinant human antibody or fragment thereof which specifically binds LEPR and a pharmaceutically acceptable carrier. In a related aspect, the invention features a composition which is a combination of an anti-LEPR antibody and a second therapeutic agent. In one embodiment, the second therapeutic agent is any agent that is advantageously combined with an anti-LEPR antibody.

In yet another aspect, the invention provides therapeutic methods for enhancing or stimulating LEPR signaling using an anti-LEPR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by stimulating or activating LEPR signaling, or otherwise mimicking the natural activity of leptin in vitro or in vivo.

Other embodiments will become apparent from a review of the ensuing detailed description.

BRIEF DESCRIPTION OF THE FIGURES

FIG. 7A shows the fat mass of mice before dosing with anti-LEPR antibodies H4H18482P2, H4H18487P2 or H4H18492P2. FIG. 7B shows the fat mass of mice treated with 30 mg/kg of H4H18482P2, H4H18487P2 or H4H18492P2.

FIG. 8 shows that anti-LEPR antibodies tested activated monkey (Mf) LEPR in an IMR-32/STAT3-luc/Mf LEPR cell line.

DETAILED DESCRIPTION OF THE INVENTION

Figure 1:
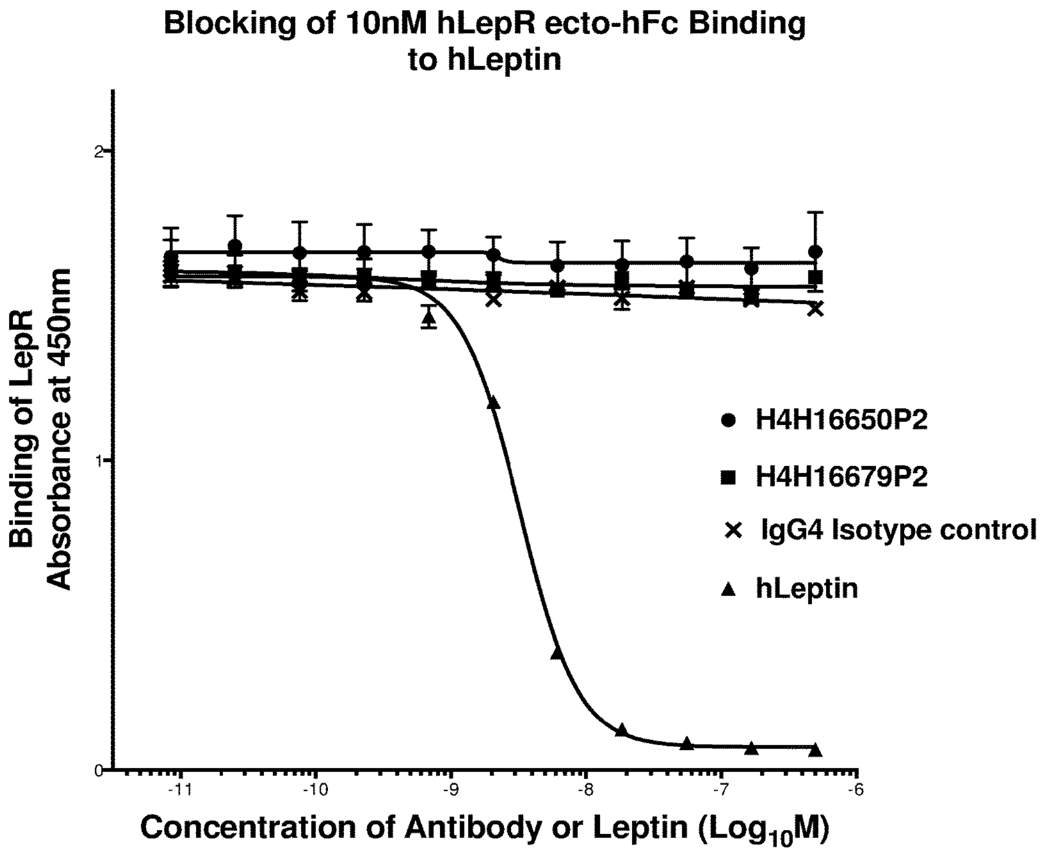
FIG. 1 depicts the binding of dimeric human LEPR to human Leptin in the presence of increasing concentrations of test anti-LEPR antibodies or control molecules, as measured by ELISA (absorbance at 450 nm).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "leptin receptor," "LEPR," and the like, as used herein, refers to the human leptin receptor, comprising the amino acid sequence as set forth in SEQ ID NO:113 (see also UniProtKB/Swiss-Prot Accession No. P48357). Alternative names for LEPR used in the scientific literature include "OB receptor," "OB-R," and "CD295." LEPR is also referred to as "WSX" (see, e.g., U.S. Pat. No. 7,524,937). The expression "LEPR" includes both monomeric and multimeric (e.g., dimeric) LEPR molecules. As used herein, the expression "monomeric human LEPR" means a LEPR protein or portion thereof that does not contain or possess any multimerizing domains and that exists under normal conditions as a single LEPR molecule without a direct physical connection to another LEPR molecule. An exemplary monomeric LEPR molecule is the molecule referred to herein as "hLEPR.mmh" comprising the amino acid sequence of SEQ ID NO:114 (see, e.g., Example 3, herein). As used herein, the expression "dimeric human LEPR" means a construct comprising two LEPR molecules connected to one another through a linker, covalent bond, non-covalent bond, or through a multimerizing domain such as an antibody Fc domain. An exemplary dimeric LEPR molecule is the molecule referred to herein as "hLEPR.mFc" comprising the amino acid sequence of SEQ ID NO:115 (see, e.g., Example 3, herein), or the molecule referred to herein as "hLEPR.hFc" comprising the amino acid sequence of SEQ ID NO:116. As used herein, expressions such "anti-LEPR antibody," "antibody that specifically binds LEPR," "LEPR-specific binding protein," and the like, unless specifically indicated otherwise, refer to molecules that bind full length human LEPR, monomeric human LEPR, dimeric human LEPR, or other constructs that comprise or consist of the LEPR extracellular domain.

All references to proteins, polypeptides and protein fragments herein are intended to refer to the human version of the respective protein, polypeptide or protein fragment unless explicitly specified as being from a non-human species. Thus, the expression "LEPR" means human LEPR unless specified as being from a non-human species, e.g., "mouse LEPR," "monkey LEPR," etc.

As used herein, the expression "cell surface-expressed LEPR" means one or more LEPR protein(s), or the extracellular domain thereof, that is/are expressed on the surface of a cell in vitro or in vivo, such that at least a portion of a LEPR protein is exposed to the extracellular side of the cell membrane and is accessible to an antigen-binding portion of an antibody. A "cell surface-expressed LEPR" can comprise or consist of a LEPR protein expressed on the surface of a cell which normally (e.g., in the native or wild-type state) expresses LEPR protein. Alternatively, "cell surface-expressed LEPR" can comprise or consist of LEPR protein expressed on the surface of a cell that normally does not express human LEPR on its surface but has been artificially engineered to express LEPR on its surface.

As used herein, the expressions such as "anti-LEPR antibody," or "antibody that binds human leptin receptor," include both monovalent antibodies with a single specificity, as well as bispecific antibodies comprising a first arm that binds LEPR and a second arm that binds a second (target) antigen, wherein the anti-LEPR arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., LEPR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-LEPR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments of the invention, the anti-LEPR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes variants of the anti-LEPR antibodies disclosed herein comprising one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention includes anti-LEPR antibodies and antigen-binding fragments thereof that comprise amino acid sequences that are substantially similar or substantially identical to one or more variable domain or CDR amino acid sequences as found in any of the exemplary anti-LEPR antibodies disclosed herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Anti-LEPR Antibodies Comprising Fc Variants

According to certain embodiments of the present invention, anti-LEPR antibodies are provided comprising an Fc domain comprising one or more mutations which enhance or diminish antibody binding to the FcRn receptor, e.g., at acidic pH as compared to neutral pH. For example, the present invention includes anti-LEPR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-LEPR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The anti-LEPR antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Biological Characteristics of the Antibodies

The present invention includes antibodies and antigen-binding fragments thereof that bind human LEPR and activate LEPR signaling. Such antibodies may be referred to herein as "agonist antibodies." In the context of the present invention, "activation of LEPR signaling" means the stimulation of an intracellular effect that normally results from the interaction of leptin with LEPR in cells that express LEPR. In certain embodiments, "activation of LEPR signaling" means the transcriptional activation of STAT3, which can be detected using any method that can measure or identify, directly or indirectly, STAT3 activity, e.g., using a labeled version of STAT3 expressed in a reporter cell line. For example, the present invention includes antibodies and antigen-binding fragments thereof that activate LEPR signaling in a cell-based reporter assay, e.g., using a cell based assay format as defined in Example 7 herein, or a substantially similar assay. Cell-based reporter assays that detect LEPR activation, such as the assay set forth in Example 7 herein, can produce a detectable signal that may be expressed in terms of an $EC_{50}$ value (i.e., the antibody concentration required to produce half-maximal signaling) and/or a percentage of the maximal signaling observed in the presence of leptin. In certain exemplary embodiments of the present invention, anti-LEPR antibodies are provided that activate LEPR signaling with an $EC_{50}$ value of less than about 12.0 nM in a cell-based reporter assay, e.g., using an assay format as defined in Example 7 herein, or a substantially similar assay. In certain exemplary embodiments of the present invention, anti-LEPR antibodies are provided that activate LEPR signaling with maximum percent activation relative to leptin signaling of greater than about 65% in a cell-based reporter assay, e.g., using an assay format as defined in Example 7 herein, or a substantially similar assay.

The present invention includes antibodies and antigen-binding fragments thereof that bind monomeric human LEPR with high affinity. For example, the present invention includes anti-LEPR antibodies that bind monomeric human LEPR (e.g., hLEPR.mmh, SEQ ID NO:114) with a $K_D$ of less than about 150 nM as measured by surface plasmon resonance at 25° C. or 37° C., e.g., using an assay format as defined in Example 3 herein, or a substantially similar assay. According to certain embodiments, anti-LEPR antibodies are provided that bind monomeric human LEPR at 25° C. with a $K_D$ of less than about 150 nM, less than about 140 nM, less than about 130 nM, less than about 120 nM, less than about 110 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, or less than about 300 pM, as measured by surface plasmon resonance, e.g., using an assay format as defined in Example 3 herein, or a substantially similar assay.

The present invention also includes antibodies and antigen-binding fragments thereof that bind monomeric human LEPR (e.g., hLEPR.mmh, SEQ ID NO:114) with a dissociative half-life (t½) of greater than about 50 minutes as measured by surface plasmon resonance at 25° C. or 37° C., e.g., using an assay format as defined in Example 3 herein, or a substantially similar assay. According to certain embodiments, anti-LEPR antibodies are provided that bind monomeric human LEPR at 25° C. with a t½ of greater than about 50 minutes, greater than about 55 minutes, greater than about 60 minutes, greater than about 65 minutes, or longer, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:115) with high affinity. For example, the present invention includes anti-LEPR antibodies that bind dimeric human LEPR with a $K_D$ of less than about 1.5 nM as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a $K_D$ of less than about 150 nM, less than about 130 nM, less than about 110 nM, less than about 80 nM, less than about 70 nM, less than about 60 nM, less than about 50 nM, less than about 40 nM, less than about 30 nM, less than about 20 nM, or less than about 10 nM, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:115) with a dissociative half-life (t½) of greater than about 10 minutes as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a t½ of greater than about 10, greater than about 15 minutes, greater than about 20 minutes, greater than about 25 minutes, greater than about 30 minutes, greater than about 40 minutes, greater than about 50 minutes, greater than about 60 minutes, greater than about 70 minutes, or longer, as measured by surface plasmon resonance, e.g., using an assay format as defined in Example 3 herein, or a substantially similar assay.

The present invention also includes antibodies and antigen-binding fragments thereof that bind LEPR in complex with human leptin ("LEPR in complex with human leptin" may also be represented by the expression "leptin:LEPR"). For example, the present invention includes antibodies and antigen-binding fragments thereof that are capable of binding to a pre-formed complex comprising hLEPR and human leptin. That is, according to certain embodiments, the interaction between anti-LEPR antibodies and LEPR is not inhibited by the presence of leptin in complex with LEPR; likewise, the interaction between leptin and LEPR, according to this aspect of the invention, is not inhibited by the presence of an anti-LEPR antibody. An exemplary assay format for determining whether an antibody or antigen-binding fragment thereof binds to LEPR in complex with human leptin is set forth in Example 4 herein.

Similarly, the present invention also includes antibodies and antigen-binding fragments thereof that bind LEPR and do not block the LEPR:leptin interaction. For example, the present invention includes antibodies and antigen-binding fragments thereof that are capable of binding LEPR, thereby producing an antibody:LEPR complex, wherein the resulting antibody:LEPR complex is capable of interacting with leptin to produce a three-member complex comprising the antibody, LEPR and leptin. An exemplary assay format for determining whether an antibody or antigen-binding fragment thereof is capable of binding LEPR in a manner that does not block or interfere with the interaction between LEPR and leptin is set forth in Example 5 herein.

The present invention also includes antibodies and antigen-binding fragments thereof that bind cell surface-expressed LEPR in the presence and/or absence of human leptin. Cell surface-expressed LEPR means LEPR or a portion thereof (e.g., an extracellular portion of LEPR) expressed on the surface of a cell, either naturally or in an engineered cell line, such that an antibody or antigen-binding fragment thereof is capable of binding to the LEPR molecule. In certain embodiments, cell surface-expressed LEPR includes recombinant complexes comprising an extracellular domain of LEPR connected to a cell via a tag or anchor (e.g., a GPI anchor as illustrated in Example 6 herein). According to this aspect of the invention, antibodies are provided which are capable of binding cell surface-expressed LEPR in the absence of leptin, and are also capable of binding cell surface-expressed LEPR in the presence of leptin (i.e., under circumstances wherein leptin is capable of binding to cell surface-expressed leptin). That is, according to certain embodiments, the interaction between anti-LEPR antibodies and cell surface-expressed LEPR is not inhibited by the presence of leptin in complex with cell surface-expressed LEPR. Antibodies according to this aspect of the invention are capable of forming a three-member complex on the surface of a cell comprising the antibody, cell surface-expressed LEPR and leptin. An exemplary assay format for determining whether an antibody or antigen-binding fragment thereof is capable of binding cell surface-expressed LEPR in the presence and absence of human leptin is set forth in Example 6 herein.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The present invention also includes anti-LEPR antibodies comprising variants of any of the HCVR, LCVR, and/or CDR amino acid sequences disclosed herein having one or more conservative substitutions. For example, the present invention includes anti-LEPR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. In certain embodiments, the present invention provides anti-LEPR antibodies comprising variant HCVR, LCVR and/or CDR amino acid sequences relative to the sequences set forth in Table 1 herein (e.g., comprising conservative amino acid substitutions), wherein such variant antibodies nonetheless exhibit one or more functions and/or properties of the exemplary anti-LEPR antibodies disclosed herein.

The extracellular domain of human LEPR contains an N-terminal cytokine receptor homology domain (CRH-1), an immunoglobulin-like (Ig) domain, and a second CRH domain (CRH-2) that is referred to as the leptin-binding domain (LBD). (Carpenter et al. (2012) Structure 20:487-97). Furthermore, LEPR shares the greatest homology and similar extracellular domain size and organization with granulocyte colony stimulating factor (GCSF) and glycoprotein 130 (gp13). (Haniu et al. (1998) J Biol Chem 273(44): 28691-699).

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The present invention includes anti-LEPR antibodies that interact with one or more epitopes found within amino acids M1-D839 of human LEPR (SEQ ID NO: 113). As set forth in Example 11, 201 peptides from human LEPR had significantly reduced deuteration uptake when bound to antibody H4H16650P2. The peptides corresponding to amino acids 162-169 (amino acids LYVLPEVL of human LEPR, SEQ ID NO: 113) and 170-191 (amino acids EDSPLVPQK- GSF of human LEPR, SEQ ID NO: 113) had slower deuteration rates when bound to H4H16650P2, indicating that this antibody binds at least two human LEPR epitopes having the sequences LYVLPEVL or EDSPLVPQKGSF (amino acids 162-169 or 170-191, respectively of SEQ ID NO: 113).

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a LEPR protein. Alternatively, the epitope may consist of a plurality of non-contiguous amino acids (or amino acid sequences) of LEPR. In some embodiments, the epitope is located on or near the leptin-binding domain of LEPR. In other embodiments, the epitope is located at a region distinct from the leptin-binding domain of LEPR, e.g., at a location on the surface of LEPR at which an antibody, when bound to such an epitope, does not interfere with leptin binding to LEPR.

Various techniques known to persons of ordinary skill in the art can be used to identify the amino acids within an epitope recognized by a particular antibody. Exemplary techniques include, e.g., alanine scanning mutational analysis, peptide blot analysis, and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography analysis of an antibody in complex with its antigen may also be used to identify the amino acids within a polypeptide with which an antibody interacts.

The present invention further includes anti-LEPR antibodies that bind to the same epitope as any of the specific exemplary antibodies described herein (e.g. antibodies comprising any of the amino acid sequences as set forth in Table 1 herein). Likewise, the present invention also includes anti-LEPR antibodies that compete for binding to LEPR with any of the specific exemplary antibodies described herein (e.g. antibodies comprising any of the amino acid sequences as set forth in Table 1 herein).

One can determine whether an antibody binds to the same epitope as, or competes for binding with, a reference anti-LEPR antibody by using routine methods known in the art and exemplified herein. For example, to determine if a test antibody binds to the same epitope as a reference anti-LEPR antibody of the invention, the reference antibody is allowed to bind to a LEPR protein. Next, the ability of a test antibody to bind to the LEPR molecule is assessed. If the test antibody is able to bind to LEPR following saturation binding with the reference anti-LEPR antibody, it can be concluded that the test antibody binds to a different epitope than the reference anti-LEPR antibody. On the other hand, if the test antibody is not able to bind to the LEPR molecule following saturation binding with the reference anti-LEPR antibody, then the test antibody may bind to the same epitope as the epitope bound by the reference anti-LEPR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-LEPR antibody, the above-described binding methodology is performed in two orientations: In a first orientation, the reference antibody is allowed to bind to a LEPR protein under saturating conditions followed by assessment of binding of the test antibody to the LEPR molecule. In a second orientation, the test antibody is allowed to bind to a LEPR molecule under saturating conditions followed by assessment of binding of the reference antibody to the LEPR molecule. If, in both orientations, only the first (saturating) antibody is capable of binding to the LEPR molecule, then it is concluded that the test antibody and the reference antibody compete for binding to LEPR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-LEPR antibodies of the present invention can be fully human antibodies. Methods for generating monoclonal antibodies, including fully human monoclonal antibodies are known in the art. Any such known methods can be used in the context of the present invention to make human antibodies that specifically bind to human LEPR.

Using VELOCIMMUNE™ technology, for example, or any other similar known method for generating fully human monoclonal antibodies, high affinity chimeric antibodies to LEPR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-LEPR antibody. While the constant region selected may vary according to specific use, high affinity antigen-binding and target specificity characteristics reside in the variable region. In certain instances, fully human anti-LEPR antibodies are isolated directly from antigen-positive B cells.

Bioequivalents

The anti-LEPR antibodies and antibody fragments of the present invention encompass proteins having amino acid sequences that vary from those of the described antibodies but that retain the ability to bind human LEPR. Such variant antibodies and antibody fragments comprise one or more additions, deletions, or substitutions of amino acids when compared to parent sequence, but exhibit biological activity that is essentially equivalent to that of the described antibodies. Likewise, the anti-LEPR antibody-encoding DNA sequences of the present invention encompass sequences that comprise one or more additions, deletions, or substitutions of nucleotides when compared to the disclosed sequence, but that encode an anti-LEPR antibody or antibody fragment that is essentially bioequivalent to an anti-LEPR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-LEPR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-LEPR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-LEPR antibodies that bind to human LEPR but not to LEPR from other species. The present invention also includes anti-LEPR antibodies that bind to human LEPR and to LEPR from one or more non-human species. For example, the anti-LEPR antibodies of the invention may bind to human LEPR and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee LEPR. According to certain exemplary embodiments of the present invention, anti-LEPR antibodies are provided which specifically bind human LEPR and cynomolgus monkey (e.g., *Macaca fascicularis*) LEPR. Other anti-LEPR antibodies of the invention bind human LEPR but do not bind, or bind only weakly, to cynomolgus monkey LEPR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-LEPR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human LEPR, and the other arm of the immunoglobulin is specific for a second antigen. The LEPR-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-LEPR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-LEPR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC *Crit. Ref. Biomed. Eng.* 14:201). In another embodiment, polymeric materials can be used; see, Medical Applications of Controlled Release, Langer and Wise (eds.), 1974, *CRC Pres*., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-LEPR antibody (e.g., an anti-LEPR antibody comprising any of the HCVR/LCVR or CDR sequences as set forth in Table 1 herein). The therapeutic composition can comprise any of the anti-LEPR antibodies disclosed herein, or antigen-binding fragments thereof, and a pharmaceutically acceptable carrier or diluent.

The antibodies of the invention are useful, inter alia, for the treatment, prevention and/or amelioration of any disease or disorder associated with or mediated by leptin deficiency, leptin resistance, hypoleptinemia, or otherwise treatable by stimulating or activating LEPR signaling or mimicking the natural activity of leptin in vitro or in vivo. For example, the antibodies and antigen-binding fragments thereof of the present invention are useful for treating lipodystrophy conditions. Exemplary lipodystrophy conditions that are treatable by the antibodies and antigen-binding fragments of the present invention include, e.g., congenital generalized lipodystrophy, acquired generalized lipodystrophy, familial partial lipodystrophy, acquired partial lipodystrophy, centrifugal abdominal lipodystrophy, lipoatrophia annularis, localized lipodystrophy, and HIV-associated lipodystrophy.

The present invention also includes anti-LEPR antibodies and antigen-binding fragments thereof that are useful for restoring leptin signaling to cells, tissues and organs expressing one or more LEPR mutations associated with obesity. For example, certain LEPR mutants have been identified that exhibit no, or reduced signaling in the presence of leptin and are associated with obesity and related disorders. As used herein, a LEPR mutant that exhibits no signaling in the presence of leptin is referred to as a "signaling-defective LEPR mutant." An exemplary signaling-defective LEPR mutation is LEPR-A409E (Farooqi et al., 2007, *N Engl J Med* 356(3): 237-247). As used herein, a LEPR mutant that exhibits reduced signaling in the presence of leptin (as compared to wild-type LEPR) is referred to as a "signaling-impaired LEPR mutant." An exemplary signaling-impaired LEPR mutation is LEPR-P316T (Mazen et al., 2011, *Mol Genet Metab* 102:461-464). Thus, the present invention includes anti-LEPR antibodies and antigen-binding fragments thereof that are useful for the treatment, prevention and/or amelioration of diseases and disorders caused by or associated with one or more signaling-defective (e.g., A409E) and/or signaling-impaired (e.g., P316T) LEPR mutants.

The anti-LEPR antibodies and antigen-binding fragments thereof of the present invention are also useful for the treatment or prevention of one or more diseases or disorders selected from the group consisting of obesity, metabolic syndrome, diet-induced food craving, functional hypothalamic amenorrhea, type 1 diabetes, type 2 diabetes, insulin resistance, severe insulin resistance including severe insulin resistance due to mutation in insulin receptor, severe insulin resistance not caused by mutation in the insulin receptor, severe insulin resistance caused by a mutation in downstream signaling pathways or induced by other causes, non-alcoholic and alcoholic fatty liver diseases, Alzheimer's disease, leptin deficiency, leptin resistance, lipodystrophies, Leprechaunism/Donohue syndrome, Rabson-Mendenhall syndrome.

In the context of the methods of treatment described herein, the anti-LEPR antibody may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-LEPR antibodies described herein in combination with one or more additional therapeutically active components, and methods of treatment comprising administering such combinations to subjects in need thereof.

The anti-LEPR antibodies of the present invention may be co-formulated with and/or administered in combination with one or more additional therapeutically active component(s), such as. e.g., pharmaceutical products prescribed for the treatment of obesity, hypercholesterolemia, hyperlipidemia, type 2 diabetes, type 1 diabetes, appetite control, infertility, etc. Examples of such additional therapeutically active components include, e.g., recombinant human leptin (e.g., metreleptin [MYALEPT]), PCSK9 inhibitors (e.g., anti-PCSK9 antibodies [alirocumab, evolocumab, bococizumab, lodelcizumab, ralpancizumab, etc.]), statins (atorvastatin, rosuvastatin, cerivastatin, pitavastatin, fluvastatin, simvastatin, lovastatin, pravastatin, etc.), ezetimibe, insulin, insulin variants, insulin secretagogues, metformin, sulfonylureas, sodium glucose cotransporter 2 (SGLT2) Inhibitors (e.g., dapaglifozin, canaglifozin, empagliflozin, etc.), GLP-1 agonists/analogues (e.g., extendin-4, exenatide, liraglutide, lixisenatide, albiglutide, dulaglutide, etc.), glucagon (GCG) inhibitors (e.g., anti-GCG antibodies), glucagon receptor (GCGR) inhibitors (e.g., anti-GCGR antibodies, small molecule GCGR antagonists, GCGR-specific antisense oligonucleotides, anti-GCGR aptamers [e.g., Spiegelmers], etc.), angiopoietin-like protein (ANGPTL) inhibitors (e.g., anti-ANGPTL3 antibodies, anti-ANGPTL4 antibodies, anti-ANGPTL8 antibodies, etc.), Phentermine, Orlistat, Topiramate, Bupropion, Topiramate/Phentermine, Bupropion/Naltrexone, Bupropion/Zonisamide, Pramlintide/Metrelepin, Lorcaserin, Cetilistat, Tesofensine, Velneperit, etc.

The additional therapeutically active component(s), e.g., any of the agents listed above or derivatives thereof, may be administered just prior to, concurrent with, or shortly after the administration of an anti-LEPR antibody of the present invention; (for purposes of the present disclosure, such administration regimens are considered the administration of an anti-LEPR antibody "in combination with" an additional therapeutically active component). The present invention includes pharmaceutical compositions in which an anti-LEPR antibody of the present invention is co-formulated with one or more of the additional therapeutically active component(s) as described elsewhere herein.

Administration Regimens

According to certain embodiments of the present invention, multiple doses of an anti-LEPR antibody (or a pharmaceutical composition comprising a combination of an anti-LEPR antibody and any of the additional therapeutically active agents mentioned herein) may be administered to a subject over a defined time course. The methods according to this aspect of the invention comprise sequentially administering to a subject multiple doses of an anti-LEPR antibody of the invention. As used herein, "sequentially administering" means that each dose of anti-LEPR antibody is administered to the subject at a different point in time, e.g., on different days separated by a predetermined interval (e.g., hours, days, weeks or months). The present invention includes methods which comprise sequentially administering to the patient a single initial dose of an anti-LEPR antibody, followed by one or more secondary doses of the anti-LEPR antibody, and optionally followed by one or more tertiary doses of the anti-LEPR antibody.

The terms "initial dose," "secondary doses," and "tertiary doses," refer to the temporal sequence of administration of the anti-LEPR antibody of the invention. Thus, the "initial dose" is the dose which is administered at the beginning of the treatment regimen (also referred to as the "baseline dose," "loading dose," "starting dose," and the like); the "secondary doses" are the doses which are administered after the initial dose; and the "tertiary doses" are the doses which are administered after the secondary doses. The initial, secondary, and tertiary doses may all contain the same amount of anti-LEPR antibody, but generally may differ from one another in terms of frequency of administration. In certain embodiments, however, the amount of anti-LEPR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic and Analytic Uses of the Antibodies

The anti-LEPR antibodies of the present invention may also be used to detect and/or measure LEPR, or LEPR-expressing cells in a sample, e.g., for diagnostic purposes. For example, an anti-LEPR antibody, or fragment thereof, may be used to diagnose a condition or disease characterized by aberrant expression (e.g., over-expression, under-expression, lack of expression, etc.) of LEPR. Exemplary diagnostic assays for LEPR may comprise, e.g., contacting a sample, obtained from a patient, with an anti-LEPR antibody of the invention, wherein the anti-LEPR antibody is labeled with a detectable label or reporter molecule. Alternatively, an unlabeled anti-LEPR antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure LEPR in a sample include enzyme-linked immunosorbent assay (ELISA), radioimmunoassay (RIA), fluorescence-activated cell sorting (FACS), and positron emission tomography (PET) scanning.

Samples that can be used in LEPR diagnostic assays according to the present invention include any tissue or fluid sample obtainable from a patient which contains detectable quantities of LEPR protein, or fragments thereof, under normal or pathological conditions. Generally, levels of LEPR in a particular sample obtained from a healthy patient (e.g., a patient not afflicted with a disease or condition associated with abnormal LEPR levels or activity) will be measured to initially establish a baseline, or standard, level of LEPR. This baseline level of LEPR can then be compared against the levels of LEPR measured in samples obtained from individuals suspected of having a LEPR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Antigen-Binding Proteins that Specifically Bind the Leptin Receptor (LEPR)

Anti-LEPR antibodies were obtained by immunizing a VELOCIMMUNE® mouse (i.e., an engineered mouse comprising DNA encoding human immunoglobulin heavy and kappa light chain variable regions) with an immunogen comprising the extracellular domain of LEPR. The antibody immune response was monitored by a LEPR-specific immunoassay. Using previously described techniques, fully human anti-LEPR antibodies were isolated and purified.

Certain biological properties of the exemplary anti-LEPR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-LEPR antibodies of the invention. The corresponding nucleic acid sequence identifiers are set forth in Table 2.

TABLE 1

Amino Acid Sequence Identifiers

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H4H16650P2 | 2 | 4 | 6 | 8 | 10 | 12 | 14 | 16 |
| H4H16679P2 | 18 | 20 | 22 | 24 | 10 | 12 | 14 | 16 |
| H4H17319P2 | 26 | 28 | 30 | 32 | 10 | 12 | 14 | 16 |
| H4H17321P2 | 34 | 36 | 38 | 40 | 10 | 12 | 14 | 16 |

TABLE 1-continued

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H18417P2 | 42 | 44 | 46 | 48 | 10 | 12 | 14 | 16 |
| H4H18438P2 | 50 | 52 | 54 | 56 | 10 | 12 | 14 | 16 |
| H4H18445P2 | 58 | 60 | 62 | 64 | 10 | 12 | 14 | 16 |
| H4H18446P2 | 66 | 68 | 70 | 72 | 10 | 12 | 14 | 16 |
| H4H18449P2 | 74 | 76 | 78 | 80 | 10 | 12 | 14 | 16 |
| H4H18482P2 | 82 | 84 | 86 | 88 | 90 | 92 | 94 | 96 |
| H4H18487P2 | 98 | 100 | 102 | 104 | 90 | 92 | 94 | 96 |
| H4H18492P2 | 106 | 108 | 110 | 112 | 90 | 92 | 94 | 96 |

TABLE 2

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H16650P2 | 1 | 3 | 5 | 7 | 9 | 11 | 13 | 15 |
| H4H16679P2 | 17 | 19 | 21 | 23 | 9 | 11 | 13 | 15 |
| H4H17319P2 | 25 | 27 | 29 | 31 | 9 | 11 | 13 | 15 |
| H4H17321P2 | 33 | 35 | 37 | 39 | 9 | 11 | 13 | 15 |
| H4H18417P2 | 41 | 43 | 45 | 47 | 9 | 11 | 13 | 15 |
| H4H18438P2 | 49 | 51 | 53 | 55 | 9 | 11 | 13 | 15 |
| H4H18445P2 | 57 | 59 | 61 | 63 | 9 | 11 | 13 | 15 |
| H4H18446P2 | 65 | 67 | 69 | 71 | 9 | 11 | 13 | 15 |
| H4H18449P2 | 73 | 75 | 77 | 79 | 9 | 11 | 13 | 15 |
| H4H18482P2 | 81 | 83 | 85 | 87 | 89 | 91 | 93 | 95 |
| H4H18487P2 | 97 | 99 | 101 | 103 | 89 | 91 | 93 | 95 |
| H4H18492P2 | 105 | 107 | 109 | 111 | 89 | 91 | 93 | 95 |

Antibodies are typically referred to herein according to the following nomenclature: Fc prefix (e.g. "H4H," "H1M," "H2M," etc.), followed by a numerical identifier (e.g. "16650," "16679," etc.), followed by a "P" or "N" suffix. Thus, according to this nomenclature, an antibody may be referred to herein as, e.g., "H4H16650P2," "H4H16679P2," etc. The Fc prefixes on the antibody designations used herein (H4H, H1M and H2M) indicate the particular Fc region isotype of the antibody. For example, an "H4H" antibody has a human IgG4 Fc, whereas an "H1M" antibody has a mouse IgG1 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

"Comparator mAb" as used in Examples herein refers to Fab9F8 described in Fazeli et al. (2006) J Immunol Methods 312:190-200 and Carpenter et al. (2012) Structure 20(3): 487-97.

Example 3: Surface Plasmon Resonance Derived Binding Affinities and Kinetic Constants of Human Monoclonal Anti-LEPR Antibodies Equilibrium dissociation constants ($K_D$ values) for LEPR binding to purified anti-LEPR monoclonal antibodies were determined using a real-time surface plasmon resonance biosensor using a Biacore 4000 instrument. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore sensor surface was first derivatized by amine coupling with a monoclonal mouse anti-human Fc antibody (GE, # BR-1008-39) to capture anti-LEPR monoclonal antibodies. Binding studies were performed on following LEPR reagents: human LEPR extracellular domain expressed with a C-terminal myc-myc-hexahistidine tag (hLEPR.mmh; SEQ ID NO: 114), *macaca fascicularis* LEPR extracellular domain expressed with a C-terminal myc-myc-hexahistidine tag (mfLEPR.mmh; SEQ ID NO: 117), human LEPR extracellular domain expressed with a C-terminal mouse IgG2a Fc tag (hLEPR.mFc; SEQ ID NO: 115), mouse LEPR extracellular domain expressed with a C-terminal myc-myc-hexahistidine tag (mLEPR.mmh; SEQ ID NO: 118) and rat LEPR extracellular domain expressed with a C-terminal myc-myc-hexahistidine tag (rLEPR.mmh; SEQ ID NO: 119). Different concentrations of LEPR reagents were first prepared in HBS-ET running buffer (100 nM-3.7 nM; 3-fold serial dilution) and were injected over anti-human Fc captured anti-LEPR monoclonal antibody surface for 4 minutes at a flow rate of 30 µL/minute, while the dissociation of monoclonal antibody bound LEPR reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t1/2(\text{min}) = \frac{\ln(2)}{60*kd}$$

Binding kinetics parameters for hLEPR.mmh, mfLEPR.MMH or hLEPR.mFc, binding to different anti-LEPR monoclonal antibodies of the invention at 25° C. and 37° C. are shown in Tables 3 through 8.

TABLE 3

Binding kinetics parameters of hLEPR-MMH binding to LEPR monoclonal antibodies at 25° C.

| mAb Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H16650P2 | 167 ± 0.3 | 51 | 2.81E+04 | 2.23E−04 | 7.93E−09 | 52 |
| H4H16679P2 | 192 ± 0.7 | 39 | 2.34E+04 | 2.46E−04 | 1.05E−08 | 47 |
| H4H18417P2 | 163 ± 0.4 | 28 | 6.14E+04 | 7.90E−03 | 1.29E−07 | 1.5 |
| H4H18438P2 | 166 ± 0.4 | 22 | 3.00E+04 | 2.26E−03 | 7.54E−08 | 5.1 |
| H4H18445P2 | 194 ± 1.1 | 45 | 4.42E+04 | 4.78E−03 | 1.08E−07 | 2.4 |
| H4H18446P2 | 163 ± 2.4 | 16 | 1.81E+04 | 9.51E−04 | 5.25E−08 | 12 |
| H4H18449P2 | 176 ± 1.3 | 54 | 2.91E+04 | 2.35E−04 | 8.08E−09 | 49 |
| H4H18482P2 | 163 ± 0.4 | 47 | 6.31E+04 | 6.77E−03 | 1.07E−07 | 1.7 |
| H4H18487P2 | 190 ± 1.2 | 42 | 4.73E+04 | 7.03E−03 | 1.48E−07 | 1.6 |
| H4H18492P2 | 167 ± 3.1 | 87 | 8.10E+04 | 8.98E−04 | 1.11E−08 | 13 |
| H4H17319P2 | 200 ± 0.4 | 36 | 2.61E+04 | 5.29E−04 | 2.03E−08 | 22 |
| H4H17321P2 | 221 ± 0.5 | 32 | 2.36E+04 | 1.96E−04 | 8.31E−09 | 59 |
| Isotype Control mAb | 171 ± 0.4 | 4 | NB* | NB* | NB* | NB* |

*NB indicates that no binding was observed under the current experimental conditions.

TABLE 4

Binding kinetics parameters of hLEPR-MMH binding to LEPR monoclonal antibodies at 37° C.

| mAb Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H16650P2 | 210 ± 2.5 | 77 | 4.85E+04 | 9.58E−04 | 1.98E−08 | 12 |
| H4H16679P2 | 239 ± 2 | 61 | 3.84E+04 | 8.42E−04 | 2.19E−08 | 14 |
| H4H18417P2 | 206 ± 3.2 | 22 | 7.70E+04 | 1.80E−02 | 2.33E−07 | 0.6 |
| H4H18438P2 | 206 ± 2.4 | 32 | 3.38E+04 | 5.76E−03 | 1.70E−07 | 2.0 |
| H4H18445P2 | 234 ± 2 | 38 | 5.13E+04 | 1.68E−02 | 3.26E−07 | 0.7 |
| H4H18446P2 | 188 ± 3.4 | 21 | 2.12E+04 | 2.56E−03 | 1.21E−07 | 4.5 |
| H4H18449P2 | 206 ± 2.1 | 73 | 3.94E+04 | 8.15E−04 | 2.07E−08 | 14 |
| H4H18482P2 | 188 ± 0.8 | 38 | 9.53E+04 | 1.93E−02 | 2.03E−07 | 0.6 |
| H4H18487P2 | 219 ± 1.7 | 30 | 6.51E+04 | 1.86E−02 | 2.86E−07 | 0.6 |
| H4H18492P2 | 192 ± 2.2 | 93 | 1.17E+05 | 4.18E−03 | 3.59E−08 | 2.8 |
| H4H17319P2 | 264 ± 0.3 | 44 | 3.54E+04 | 3.41E−03 | 9.63E−08 | 3.4 |
| H4H17321P2 | 290 ± 0.4 | 61 | 2.95E+04 | 4.38E−04 | 1.48E−08 | 26 |
| Isotype Control mAb | 193 ± 1.5 | 6 | NB* | NB* | NB* | NB* |

*NB indicates that no binding was observed under the current experimental conditions.

TABLE 5

Binding kinetics parameters of mfLEPR.MMH binding to LEPR monoclonal antibodies at 25° C.

| mAb Captured | mAb Capture Level (RU) | 100 nM mfLEP.MMH Bound (RU) | $k_a$ (1/Ms) | $k_d$ (1/s) | $K_D$ (M) | t½ (min) |
|---|---|---|---|---|---|---|
| H4H16650P2 | 166 ± 0.6 | 93 | 6.02E+04 | 1.37E−04 | 2.27E−09 | 84 |
| H4H16679P2 | 191 ± 0.7 | 66 | 4.37E+04 | 1.41E−04 | 3.22E−09 | 82 |
| H4H18417P2 | 162 ± 0.3 | 33 | 8.83E+04 | 1.23E−02 | 1.39E−07 | 0.9 |
| H4H18438P2 | 166 ± 0.6 | 5 | IC* | IC* | IC* | IC* |
| H4H18445P2 | 193 ± 0.6 | 58 | 5.90E+04 | 4.86E−03 | 8.24E−08 | 2.4 |
| H4H18446P2 | 163 ± 2.8 | 23 | 1.93E+04 | 1.12E−03 | 5.83E−08 | 10 |
| H4H18449P2 | 175 ± 0.5 | 6 | IC* | IC* | IC* | IC* |
| H4H18482P2 | 163 ± 0.8 | 63 | 1.01E+05 | 6.74E−03 | 6.66E−08 | 1.7 |
| H4H18487P2 | 189 ± 0.5 | 59 | 7.37E+04 | 6.79E−03 | 9.21E−08 | 1.7 |
| H4H18492P2 | 165 ± 2.4 | 52 | 1.10E+05 | 1.20E−02 | 1.10E−07 | 1.0 |
| H4H17319P2 | 213 ± 0.5 | 83 | 4.00E+04 | 4.63E−04 | 1.16E−08 | 25 |
| H4H17321P2 | 236 ± 0.4 | 75 | 3.26E+04 | 1.33E−04 | 4.07E−09 | 87 |

TABLE 5-continued

Binding kinetics parameters of mfLEPR.MMH binding to LEPR monoclonal antibodies at 25° C.

| mAb Captured | mAb Capture Level (RU) | 100 nM mfLEP.MMH Bound (RU) | $k_a$ (1/Ms) | $k_d$ (1/s) | $K_D$ (M) | t½ (min) |
|---|---|---|---|---|---|---|
| Isotype Control mAb | 171 ± 0.4 | 0 | NB* | NB* | NB* | NB* |

*NB indicates that no binding was observed under the current experimental conditions.

*IC indicates that observed binding was inclusive and was unable to fit the real time binding data under the current experimental conditions.

TABLE 6

Binding kinetics parameters of mfLEPR.MMH binding to LEPR monoclonal antibodies at 37° C.

| mAb Captured | mAb Capture Level (RU) | 100 nM mfLEPR.MMH Bound (RU) | $k_a$ (1/Ms) | $k_d$ (1/s) | $K_D$ (M) | t½ (min) |
|---|---|---|---|---|---|---|
| H4H16650P2 | 204 ± 1.7 | 134 | 1.22E+05 | 7.00E−04 | 5.76E−09 | 16 |
| H4H16679P2 | 232 ± 1.1 | 104 | 6.49E+04 | 6.77E−04 | 1.04E−08 | 17 |
| H4H18417P2 | 202 ± 1.3 | 28 | 1.22E+05 | 2.63E−02 | 2.17E−07 | 0.4 |
| H4H18438P2 | 203 ± 1.3 | 7 | IC* | IC* | IC* | IC* |
| H4H18445P2 | 232 ± 0.9 | 48 | 7.17E+04 | 1.90E−02 | 2.64E−07 | 0.6 |
| H4H18446P2 | 188 ± 2.9 | 30 | 2.53E+04 | 3.54E−03 | 1.40E−07 | 3.3 |
| H4H18449P2 | 202 ± 1 | 6 | IC* | IC* | IC* | IC* |
| H4H18482P2 | 187 ± 1.2 | 52 | 1.52E+05 | 2.04E−02 | 1.34E−07 | 0.6 |
| H4H18487P2 | 216 ± 0.7 | 44 | 1.10E+05 | 1.95E−02 | 1.78E−07 | 0.6 |
| H4H18492P2 | 191 ± 1.4 | 34 | 2.34E+05 | 3.94E−02 | 1.69E−07 | 0.3 |
| H4H17319P2 | 274 ± 0.5 | 113 | 5.39E+04 | 3.24E−03 | 6.01E−08 | 3.6 |
| H4H17321P2 | 304 ± 0.7 | 143 | 4.97E+04 | 2.57E−04 | 5.18E−09 | 45 |
| Isotype Control mAb | 190 ± 1 | 1 | NB* | NB* | NB* | NB* |

*NB indicates that no binding was observed under the current experimental conditions.

*IC indicates that observed binding was inclusive and was unable to fit the real time binding data under the current experimental conditions.

TABLE 7

Binding kinetics parameters of hLEPR.mFc binding to LEPR monoclonal antibodies at 25° C.

| mAb Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H16650P2 | 165 ± 0.2 | 102 | 1.06E+05 | 8.32E−05 | 7.85E−10 | 139 |
| H4H16679P2 | 190 ± 1.2 | 78 | 5.84E+04 | 9.68E−05 | 1.66E−09 | 119 |
| H4H18417P2 | 162 ± 0.6 | 90 | 1.40E+05 | 5.63E−04 | 4.04E−09 | 21 |
| H4H18438P2 | 165 ± 1.2 | 51 | 5.19E+04 | 2.44E−04 | 4.70E−09 | 47 |
| H4H18445P2 | 192 ± 0.4 | 76 | 1.22E+05 | 4.92E−04 | 4.03E−09 | 23 |
| H4H18446P2 | 162 ± 2.8 | 20 | 3.20E+04 | 2.08E−04 | 6.48E−09 | 56 |
| H4H18449P2 | 174 ± 0.6 | 116 | 7.05E+04 | 6.82E−05 | 9.64E−10 | 169 |
| H4H18482P2 | 162 ± 0.5 | 88 | 1.44E+05 | 4.91E−04 | 3.42E−09 | 24 |
| H4H18487P2 | 188 ± 0.6 | 85 | 1.06E+05 | 6.03E−04 | 5.70E−09 | 19 |
| H4H18492P2 | 166 ± 3.2 | 129 | 2.27E+05 | 1.39E−04 | 6.13E−10 | 83 |
| H4H17319P2 | 200 ± 0.5 | 69 | 4.77E+04 | 1.64E−04 | 3.45E−09 | 70 |
| H4H17321P2 | 221 ± 0.4 | 65 | 4.10E+04 | 8.93E−05 | 2.18E−09 | 129 |
| Isotype Control mAb | 170 ± 0.7 | −2 | NB* | NB* | NB* | NB* |

*NB indicates that no binding was observed under the current experimental conditions.

TABLE 8

Binding kinetics parameters of hLEPR.mFc binding to LEPR monoclonal antibodies at 37° C.

| mAb Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H16650P2 | 199 ± 1.9 | 145 | 1.57E+05 | 2.80E−04 | 1.79E−09 | 41 |
| H4H16679P2 | 229 ± 2.3 | 116 | 1.21E+05 | 3.10E−04 | 2.56E−09 | 37 |
| H4H18417P2 | 199 ± 1.1 | 111 | 1.85E+05 | 1.05E−03 | 5.64E−09 | 11 |
| H4H18438P2 | 199 ± 0.6 | 82 | 7.02E+04 | 5.98E−04 | 8.53E−09 | 19 |
| H4H18445P2 | 229 ± 2 | 104 | 1.56E+05 | 6.08E−04 | 3.89E−09 | 19 |
| H4H18446P2 | 186 ± 2.5 | 34 | 4.27E+04 | 5.48E−04 | 1.28E−08 | 21 |
| H4H18449P2 | 198 ± 1.6 | 148 | 1.33E+05 | 1.68E−04 | 1.26E−09 | 69 |
| H4H18482P2 | 185 ± 1.3 | 109 | 1.89E+05 | 7.26E−04 | 3.84E−09 | 16 |
| H4H18487P2 | 215 ± 1.5 | 99 | 1.23E+05 | 6.06E−04 | 4.93E−09 | 19 |
| H4H18492P2 | 189 ± 1.8 | 160 | 4.33E+05 | 5.00E−04 | 1.16E−09 | 23 |
| H4H17319P2 | 262 ± 0.5 | 100 | 8.51E+04 | 6.52E−04 | 7.66E−09 | 18 |
| H4H17321P2 | 289 ± 0.4 | 110 | 5.53E+04 | 1.74E−04 | 3.15E−09 | 66 |
| Isotype Control mAb | 188 ± 0.8 | 1 | NB* | NB* | NB* | NB* |

*NB indicates that no binding was observed under the current experimental conditions.

At 25° C., anti-LEPR monoclonal antibodies bound to hLEPR-MMH with $K_D$ values ranging from 7.93 nM to 148 nM, as shown in Table 5. At 37° C., anti-LEPR monoclonal antibodies bound to hLEPR-MMH with $K_D$ values ranging from 14.8 nM to 326 nM, as shown in Table 4.

Ten out of 12 anti-LEPR monoclonal antibodies of the invention bound to mfLEPR.MMH. At 25° C., anti-LEPR monoclonal antibodies bound to mfLEPR.MMH with $K_D$ values ranging from 2.27 nM to 139 nM, as shown in Table 7. At 37° C., anti-LEPR monoclonal antibodies bound to mfLEPR.MMH with $K_D$ values ranging from 5.18 nM to 264 nM, as shown in Table 8.

At 25° C., anti-LEPR monoclonal antibodies bound to hLEPR-mFc with $K_D$ values ranging from 613 pM to 5.7 nM, as shown in Table 7. At 37° C., anti-LEPR monoclonal antibodies bound to hLEPR-mFc with $K_D$ values ranging from 1.16 nM to 12.8 nM, as shown in Table 8.

None of the anti-LEPR monoclonal antibodies of the invention bound to mLEPR.MMH or rLEPR.MMH at 25° C. or at 37° C. (data not shown).

Example 4. Anti-LEPR Antibodies of the Invention Bind LEPR in the Presence of Leptin: LEPR Binding Blocking of anti-LEPR antibodies from binding to LEPR by human Leptin was evaluated using a real-time surface plasmon resonance biosensor on a Biacore T200 instrument. The entire study was performed in 10 mM HEPES pH 7.4, 150 mM NaCl, 3 mM EDTA, and 0.05% v/v Surfactant Tween-20 (HBS-ET running buffer) at 25° C. The Biacore CM5 sensor surface was first derivatized by amine coupling human Leptin (R&D Systems, #398-LP) using standard EDC/NHS surface chemistry. A complex of human LEPR and human Leptin, was formed by injecting 20 nM of human LEPR extracellular domain expressed with a C-terminal myc-myc-hexahistidine tag (hLEPR-MMH; SEQ ID NO: 114), over the human Leptin immobilized Biacore sensor surface at a flow rate of 10 μL/minute or 25 μL/minute for 4 minutes, to achieve a binding response of approximately 200 RU. To evaluate whether antibody binding to hLEPR-MMH is blocked by human Leptin, 200 nM of anti-LEPR monoclonal antibodies were injected over the preformed hLEPR-MMH:human Leptin complex, at a flow rate of 50 μL/minute or 25 μL/minute for 4-5 minutes. All of the anti-LEPR antibodies of this invention that were tested bound to the complex of hLEPR-MMH and human Leptin ("Leptn;LEPR") with nearly similar signal strength and the observed binding, expressed in RUs, are reported in Table 9. This result indicates that human Leptin does not block the binding of hLEPR-MMH to anti-LEPR antibodies tested.

TABLE 9

Binding of anti-LEPR monoclonal antibodies to the pre-complex of hLEPR-MMH and human Leptin.

| Antibody | hLEPR-MMH Bound (RU) | 200 nM mAb Bound (RU) |
|---|---|---|
| H4H16650P2 | 196 | 81 |
| H4H16679P2 | 195 | 90 |
| H4H17319P2 | 196 | 92 |

Example 5. Human Leptin Receptor Blocking ELISA

For the ELISA, human Leptin (hLeptin; R&D Systems, #398-LP-01M) was coated at a concentration of 5 μg/mL in PBS on a 96-well microtiter plate overnight at 4° C. Non-specific binding sites were subsequently blocked using a 0.5% (w/v) solution of BSA in PBS. A constant amount of 10 nM of extracellular domain portion of LEPR protein that was expressed with a C-terminal human Fc tag (hLEPR.hFc; SEQ ID NO: 116) was titrated with anti-LEPR antibodies, hLeptin protein, or an isotype control antibody ranging from 8.5 pM to 500 nM in serial dilution. These antibody-protein or protein-protein complexes were then incubated for 1.5 hour at room temperature (RT). Complexes were subsequently transferred to microtiter plates coated with hLeptin and incubated for 2 hours at RT, the wells were washed, and plate-bound hLEPR.hFc was detected with an anti-human IgG polyclonal antibody conjugated with horseradish peroxidase (Jackson ImmunoResearch Inc, #109-035-098).

Samples were developed with a TMB solution (BD Biosciences, #555214; substrate A and B mixed at 1:1 ratio as per manufacturer's instructions) to produce a colorimetric reaction and then neutralized with 1M sulfuric acid before measuring absorbance at 450 nm on a Victor X5 plate reader.

Data analysis was performed using a sigmoidal dose-response model within Prism™ software (Graph Pad). Percent blockade at maximum concentration of the antibody tested was calculated as an indicator of the ability of the antibodies to block the binding of 10 nM of hLEPR.hFc to human Leptin on the plate. In the calculation, binding signal of 10 nM of hLEPR.hFc without the presence of the antibody was referenced as 100% binding or 0% blocking; and the baseline signal of buffer alone without the presence of hLEPR.hFc was referenced as 0% binding or 100% blocking. The blocking data at 500 nM antibody concentration is summarized in Table 10.

As shown in Table 10, none of the anti-LEPR antibodies of the invention demonstrated >28% blocking of the binding of hLEPR.hFc to the hLeptin coated surface. However, the Comparator Antibody and the hLeptin, as the positive control, were able to block 99% of the hLEPR.hFc binding to the hLeptin coated surface. The isotype control antibody demonstrated no measurable blocking at concentrations up to 500 nM.

TABLE 10

ELISA blocking of hLEPR.hFc binding to hLeptin by anti-LEPR antibodies

| Antibody | 500 nM Ab Blocking of 10 nM hLEPR.hFc Binding to hLeptin (% blockade) |
|---|---|
| H4H18487P2 | 5 |
| H4H18417P2 | 16 |
| H4H18482P2 | 25 |
| H4H18492P2 | −3 |
| H4H18445P2 | 28 |
| H4H18446P2 | −5 |
| H4H18449P2 | 8 |
| H4H18438P2 | 15 |
| H4H16650P2 | −7 |
| H4H16679P2 | 7 |
| H4H17319P2 | 9 |
| H4H17321P2 | 6 |
| Controls | |
| Isotype control antibody | −3 |
| Human Leptin | 99 |
| Comparator Antibody | 99 |
| Mouse IgG2a Isotype control | 32 |

Example 6. Cell Binding by FACS Analysis with HEK293/Mycx2-hLepR(ecto)-GPI Anchored Cells Leptin receptor, LEPR, is a single-pass transmembrane receptor of the class I cytokine receptor family (Tartaglia et al. (1997) *J Biol Chem* 7:272(10):6093-6). LEPR can bind to Leptin, a protein predominantly expressed by adipose tissue that is involved in regulation of food intake and metabolism (Friedman et al. (2014) *J Endocrinol* 223(1):T1-8).

In order to assess cell binding by anti-LEPR antibodies HEK293 stable cell lines were generated. One cell line, known hereafter as HEK293/hLEPR-GPI, stably expressed the extracellular domain of human LEPR (amino acids 22-839 of accession # P48357 (SEQ ID NO:113), Isoform B) with an N-terminal myc-myc tag and C-terminal peptide sequence from human carboxypeptidase M that guides the addition of GPI (Glycosylphosphatidylinositol) (Deddish et al. (1990) *J. Biological Chemistry* 265:25:15083-89) such that the protein can be GPI-anchored to the membrane. Another HEK293 cell line was generated to stably express the full length human LEPR (amino acids 1-1165 of accession # P48357 (SEQ ID NO:113), Isoform B) along with a luciferase reporter (Stat3-luciferase, Stat3-luc, SA Bioscience, #CLS-6028L), and is known hereafter as HEK293/Stat3-luc/hLEPR-FL. HEK293 cells with the Stat3-luciferase reporter only (HEK293/Stat3-luc) were also generated as a control cell line.

For the FACS analysis, HEK293 parental cells and HEK293/hLEPR-GPI cells were dissociated and plated onto 96-well v-bottom plates at $5\times10^5$ cells/well in PBS containing 2% FBS (FACS buffer). In order to test whether the ability of anti-hLEPR antibodies to bind to cells is affected by the presence of Leptin, FACS buffer with or without 1 μM human Leptin (R&D Systems, #398-LP) was incubated with the cells for 30 minutes at 4° C., followed by the addition of anti-LEPR antibodies or control antibodies at 10 nM in FACS buffer. The cells were subsequently incubated for 30 minutes at 4° C., followed by washing and then incubation with 16 μg/mL of Alexa Fluor®-647 conjugated secondary antibody (Jackson ImmunoResearch Laboratories Inc., #109-547-003) for 30 minutes at 4° C. Cells were subsequently fixed using BD CytoFix™ (Becton Dickinson, #554655), filtered, and analyzed on a HyperCyt Flow Cytometer (Beckman Coulter). Unstained and secondary antibody alone controls were also tested for all cell lines. The results were analyzed using ForeCyt (IntelliCyt) and FlowJo version 10 software to determine the geometric means of fluorescence for viable cells. The geometric mean of fluorescence for each sample was then normalized to the geometric mean of unstained cells to obtain relative binding per condition referred to as "binding ratios", and these binding ratios were recorded for each antibody tested.

As shown in Table 11, 9 anti-LEPR antibodies of the invention tested at 10 nM demonstrated binding to HEK293/hLEPR-GPI cells with binding ratios ranging from 824 to 3374 fold without Leptin. The anti-LEPR antibodies also bound in the presence of 1 μM Leptin with binding ratios of 398 and 4184 fold. As shown in Table 11, the Comparator Antibody tested at 10 nM demonstrated binding to HEK293/hLEPR-GPI cells with a binding ratio of 2349-fold without Leptin but showed significantly less binding to cells in the presence of 1 μM Leptin with binding ratio of 112. The anti-LEPR antibodies did not demonstrate any significant binding to the HEK293 parental cells with binding ratios with and without 1 μM Leptin ranging from 1 to 9 fold. The isotype control antibodies and secondary antibodies alone samples also did not demonstrate significant binding to either cell line with or without Leptin, with binding ratios ranging from 1 to 6 fold.

As shown in Table 12, four antibodies of the invention tested at 70 nM without Leptin, demonstrated binding to HEK293/hLEPR-GPI cells with binding ratios ranging from 707 to 1131 fold and to HEK293/Stat3-luc/hLEPR-FL cells with binding ratios ranging from 42 to 51. The anti-LEPR antibodies did not demonstrate any significant binding to the HEK293/Stat3-luc cells with binding ratios ranging from 1 to 8 fold. The isotype control antibodies and secondary antibodies alone samples also did not demonstrate significant binding to any of the cell lines tested, with binding ratios ranging from 1 to 2 fold.

TABLE 11

Binding of 10 nM anti-LEPR antibodies to HEK293/hLEPR-GPI and HEK293 parental cells +/−1 μM Human Leptin

| Antibody | Binding Ratio: Normalized to Unstained Sample of Each Cell Line | | | | |
|---|---|---|---|---|---|
| | No added Leptin | | 1 μM Leptin | | |
| | HEK293 parental | HEK293/ hLEPR-GPI | HEK293 parental | HEK293/ hLEPR-GPI | Antibody Type |
| H4H16650P2 | 5 | 2420 | 4 | 3124 | Agonist |
| H4H16679P2 | 5 | 2058 | 8 | 2223 | Agonist |
| H4H18417P2 | 1 | 1835 | 2 | 2604 | Potentiator |
| H4H18438P2 | 2 | 1486 | 3 | 2414 | Potentiator |
| H4H18445P2 | 2 | 2016 | 3 | 2488 | Potentiator |
| H4H18449P2 | 5 | 3374 | 9 | 3113 | Potentiator |
| H4H18482P2 | 1 | 1966 | 3 | 2704 | Potentiator |
| H4H18487P2 | 1 | 2422 | 3 | 2670 | Potentiator |
| H4H18492P2 | 3 | 2603 | 7 | 4184 | Potentiator |
| Comparitor | 6 | 2349 | 3 | 112 | N/A |
| Isotype control antibody | 1 | 6 | 2 | 4 | N/A |
| Secondary antibody alone | 1 | 3 | 2 | 3 | N/A |
| Unstained | 1 | 1 | 1 | 1 | N/A |

*Classification of antibodies as "Agonist" or "Potentiator" is based in part on the results observed in Examples 7 and 8 herein.

TABLE 12

Binding of 70 nM anti-LEPR antibodies to HEK293/hLEPR-GPI, HEK293/Stat3-hLEPR-FL, and HEK293/Stat3-luc parental cells

| Antibody | Binding Ratio: Normalized to Unstained Sample of Each Cell Line | | | |
|---|---|---|---|---|
| | HEK293/ Stat3-luc | HEK293/ hLEPR-GPI | HEK293/ Stat3-luc hLEPR-FL | Antibody Type |
| H4H16650P2 | 6 | 707 | 42 | Agonist |
| H4H16679P2 | 8 | 1078 | 51 | Agonist |
| H4H17319P2 | 7 | 1131 | 47 | Agonist |
| H4H17321P2 | 7 | 1126 | 46 | Agonist |
| Isotype control antibody | 2 | 2 | 2 | |
| Secondary antibody alone | 1 | 1 | 1 | |
| Unstained | 1 | 1 | 1 | |

Example 7. Anti-LEPR Antibodies of the Invention Activate LEPR Signaling in the Presence or Absence of Leptin A bioassay was developed to detect the transcriptional activation of STAT3 via LEPR activation using a reporter cell line that stably expresses full-length human LEPR (hLEPR; amino acids 1 through 1165 of accession number NP_002294.2) along with a luciferase reporter (STAT3-Luc; Qiagen, # CLS-6028L) in an IMR-32 cell line, a human neuroblastoma cell line. The resulting stable cell line, referred to as IMR-32/STAT3-Luc/hLEPR, was isolated and maintained in MEM-Earl medium supplemented with 10% FBS, NEAA, 1 ug/mL Puromycin, 100 ug/mL of Hygromycin B and Penicillin/Streptomycin/L-Glutamine (Complete Medium).

The resulting bioassay was used to measure the effect of anti-LEPR antibodies of the invention on LEPR signaling in the presence or absence of Leptin. For the bioassay, IMR-32/STAT3-Luc/hLEPR cells were plated at the density of 20,000 cells/100 ul/well for 96 well format in the complete medium, and the following day replaced with the appropriate volume of Opti-MEM medium supplemented with 1% BSA and 0.1% FBS (Assay Buffer) for 30 minutes. To measure the effect of the antibodies of the invention in the absence of Leptin, the anti-LEPR antibodies or an isotype control antibody and human Leptin (hLeptin; R&D Systems, #398-LP) were half-log serially diluted to final concentrations ranging from 100 nM to 300 fM in Assay Buffer, which were added to the cells and subsequently incubated overnight at 37° C. in 5% CO2.

To measure the effect of the antibodies of the invention in the presence of Leptin, a fixed concentration of human Leptin at 200 pM in Assay Buffer was added to the cells, immediately followed by the addition of anti-LEPR antibodies or isotype control antibody that were half-log serially diluted to final concentrations ranging from 100 nM to 300 fM. The samples were then incubated overnight at 37° C. in 5% CO2. OneGlo reagent (Promega, # E6051) was then added to the samples and luciferase activity was measured on an Envision Multilable Plate Reader (Perkin Elmer) in Luminescent mode. The relative light unit (RLU) values were obtained and the results were analyzed using nonlinear regression with GraphPad Prism software (GraphPad). The maximum RLU value obtained from the hLeptin dose response was defined as 100% activation in the IMR-32/STAT3-Luc/hLEPR assay.

As shown in Table 13, in Study 1, in the absence of hLeptin, all of the anti-LEPR antibodies tested demonstrated weak stimulation of the IMR-32/STAT3-Luc/hLEPR cells with $EC_{50}$ values ranging from 134 pM to 11.9 nM and maximal activation ranging from 5% to 13% respectively that of maximum activation obtained from the hLeptin dose response. In Study 2, in the absence of hLeptin, the 4 anti-LEPR antibodies tested demonstrated stimulation of the IMR-32/STAT3-Luc/hLEPR cells with $EC_{50}$ values ranging from 61.9 pM to 206.9 pM and maximal activation ranging from 65% to 68% respective to the maximum activation obtained from the hLeptin dose response. In Study 1, in the presence of 200 pM of hLeptin, all of the anti-LEPR antibodies tested demonstrated stimulation of the IMR-32/STAT3-Luc/hLEPR cells with $EC_{50}$ values ranging from 20.2 pM to 523 pM and maximal activation ranging from 66% to 107% respectively that of maximum activation obtained from the hLeptin dose response. Because these antibodies enhanced leptin-induced LEPR signaling, these antibodies were classified as "potentiators", as defined herein. In Study 2, in the presence of 200 pM of hLeptin, the 4 anti-LEPR antibodies tested demonstrated stimulation of the IMR-32/STAT3-Luc/hLEPR cells with $EC_{50}$ values ranging from 51.9 pM to 257.3 pM with maximal activation ranging from 76% to 88% that of maximum activation obtained from the hLeptin dose response. LEPR signaling was not appreciably enhanced by these antibodies in the presence of leptin. The isotype control antibody did not demonstrate any measurable stimulation of the IMR-32/STAT3-Luc/hLEPR cells in any of the assays.

TABLE 13

Activation of hLEPR by anti-LEPR Antibodies

| | IMR-32/LEPR without human Leptin | | IMR-32/LEPR with 200pM human Leptin | |
|---|---|---|---|---|
| Antibody | $EC_{50}$ (M) | % activation | $EC_{50}$ (M) | % activation |
| Study 1 | | | | |
| H4H18445P2 | 1.19E−08 | 5 | 4.10E−10 | 97 |
| H4H18446P2 | 3.73E−10 | 6 | 3.42E−11 | 68 |
| H4H18449P2 | 2.12E−10 | 13 | 5.23E−11 | 66 |
| H4H18438P2 | 1.49E−09 | 5 | 2.02E−11 | 76 |
| H4H18482P2 | 2.69E−10 | 7 | 1.69E−10 | 94 |
| H4H18487P2 | 8.01E−10 | 6 | 4.10E−10 | 107 |
| H4H18492P2 | 1.34E−10 | 5 | 2.74E−11 | 94 |
| H4H18417P2 | 1.53E−10 | 5 | 5.23E−10 | 87 |
| Study 2 | | | | |
| H4H16650P2 | 6.19E−11 | 68 | 5.19E−11 | 88 |
| H4H16679P2 | 8.62E−11 | 65 | 7.37E−11 | 88 |
| H4H17319P2 | 1.867E−10 | 68 | 1.914E−10 | 76 |
| H4H17321P2 | 2.069E−10 | 66 | 2.573E−10 | 76 |

Example 8. Anti-LEPR Antibodies of the Invention Activate Signaling in Cells Expressing Signaling-Defective or Signaling-Impaired LEPR Mutants LEPR mutants have been identified that exhibit defective or impaired leptin-mediated signaling and are associated with early-onset obesity. For example, LEPR-A409E is a signaling-defective mutant LEPR protein that does not transduce leptin signals to STAT3; the A409E mutant was originally identified as a monogenic cause of early onset obesity. (Farooqi et al., 2007, *N Engl J Med* 356(3): 237-247). LEPR-P316T is a signaling-impaired mutant LEPR protein that has also been shown to be associated with early-onset obesity. (Mazen et al., 2011, *Mol Genet Metab* 102:461-464).

In this Example, the ability of anti-LEPR antibodies of the invention to stimulate LEPR signaling in cell lines expressing signaling-defective or signaling-impaired LEPR mutants was assessed. In particular, reporter cell lines (HEK293) were constructed expressing either wild-type LEPR, LEPR-A409E (signaling-defective) or LEPR-P316T (signaling-impaired). Cells were treated with either vehicle only, recombinant human leptin, control IgG, or agonist anti-LEPR antibodies of the present invention (H4H16650 or H4H16679), and the extent of LEPR signaling (as measured by Western blot detection of pSTAT3-Y705 expression relative to STAT3 expression) was determined.

Figure 2A:
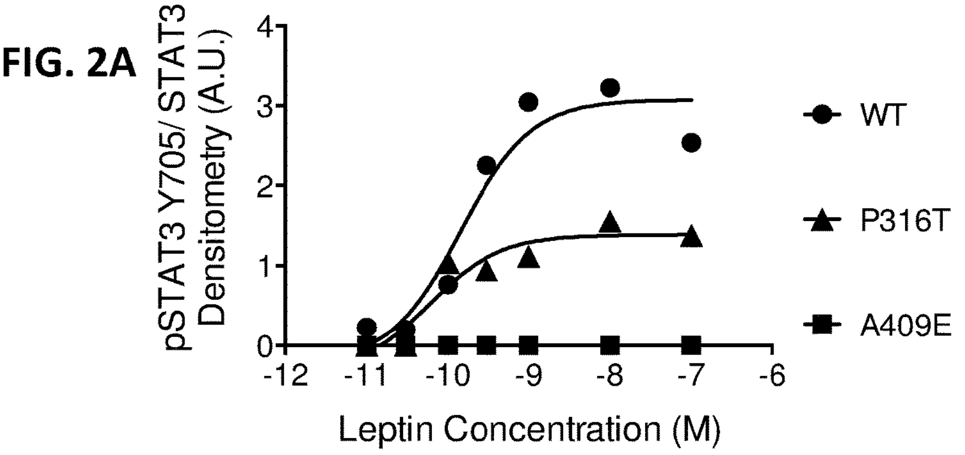
FIGS. 2A-2C illustrates the extent of LEPR signaling in HEK293 cells expressing either wild-type LEPR (circles), a signaling-defective LEPR mutant (A409E, squares), or a signaling-impaired LEPR mutant (P316T, triangles). LEPR signaling is expressed as ratio of pSTAT3-Y705/STAT3, measured by densitometry from Western blots prepared from cells treated with increasing concentrations of leptin (FIG. 2A), H4H16650 (FIG. 2B), or H4H16679 (FIG. 2C).
Figure 2B:
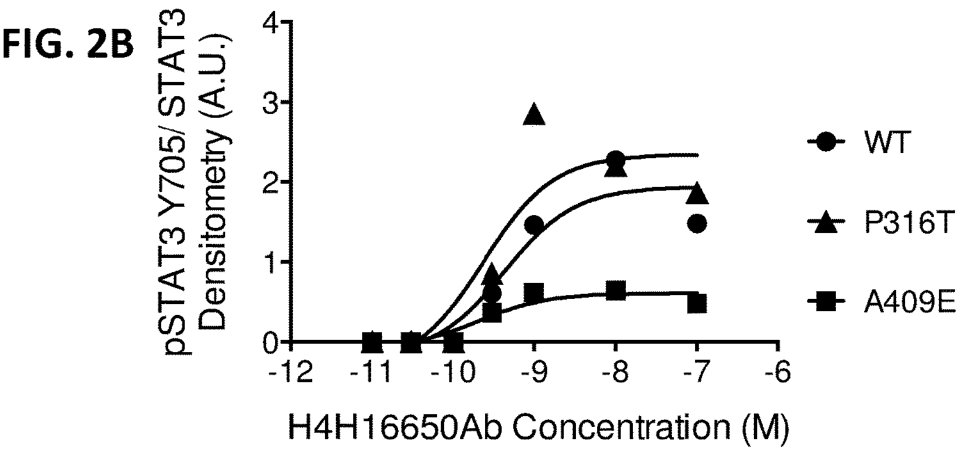
Figure 2C:
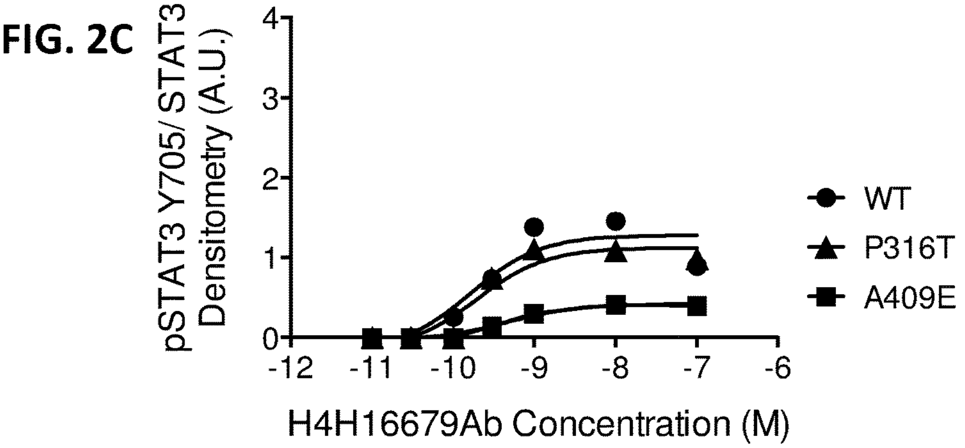

The agonist anti-LEPR antibodies of the present invention (H4H16650 and H4H16679) were shown in these experiments to stimulate LEPR signaling in cells expressing the LEPR-A409E mutant or the LEPR-P316T mutant (as measured by STAT3 expression) in a dose-dependent manner (FIG. 2, panels B and C). By contrast, leptin treatment induced only modest signaling in cells expressing the LEPR-P316T mutant, and no signaling in cells expressing the LEPR-A409E mutant. (FIG. 2, panel A). Moreover, no LEPR signaling was detected in any of the cell lines treated with vehicle or IgG control antibody (data not shown). Other signaling-defective or signaling-impaired LEPR mutants were tested in this assay but were not activated by anti-LEPR mutants (data not shown), suggesting that this rescue effect may be mutant-dependent.

The results of this Example indicate that the agonist anti-LEPR antibodies of the present invention may be useful in the treatment of diseases and disorders (e.g., early-onset obesity) that are caused by or associated with certain signaling-defective or signaling-impaired LEPR mutants (e.g., LEPR-P316T or LEPR-A409E).

Example 9: Octet Cross-Competition Between Different Anti-LEPR Monoclonal Antibodies Binding competition between a panel of different anti-LEPR monoclonal antibodies was determined using a real time, label-free bio-layer interferometry assay on the Octet HTX biosensor platform (Pall ForteBio Corp.). The entire experiment was performed at 25° C. in buffer containing 10 mM HEPES, 150 mM NaCl, 3 mM EDTA, and 0.05% v/v Surfactant Tween-20, 1 mg/mL BSA, pH 7.4 (HBS-EBT) with the plate shaking at the speed of 1000 rpm. To assess whether two antibodies were able to compete with one another for binding to their respective epitopes on recombinant human LEPR expressed with a C-terminal myc-myc-hexahistidine tag (hLEPR.mmh; SEQ ID NO: 114), around 0.25 nm or 0.34 nm of hLEPR-MMH was first captured onto anti-penta-His antibody coated Octet biosensor tips (Fortebio Inc, #18-5122) by submerging the biosensor tips for 5 minutes in wells containing 20 μg/mL of hLEPR-MMH. The antigen captured biosensor tips were then saturated with a first anti-LEPR monoclonal antibody (subsequently referred to as mAb-1) by dipping into wells containing 50 μg/mL solution of mAb-1 for 210 seconds. The biosensor tips were then subsequently dipped into wells containing a 50 μg/mL solution of a second anti-LEPR monoclonal antibody (subsequently referred to as mAb-2) for 150 seconds. The biosensor tips were washed in HBS-EBT buffer in between every step of the experiment. The real-time binding response was monitored during the entire course of the experiment and the binding response at the end of every step was recorded. The response of mAb-2 binding to hLEPR-MMH pre-complexed with mAb-1 was compared and competitive/non-competitive behavior of different anti-LEPR monoclonal antibodies was determined as shown in Table 14 and Table 15.

TABLE 14

| Cross-competition between anti-LEPR monoclonal antibodies | |
|---|---|
| First antibody (mAb-1) binding to captured hLEPR-MMH | Second antibody (mAb-2) shown to compete with mAb-1 |
| H4H18492P2 | H4H18417P2 |
| | H4H18438P2 |
| H4H18417P2 | H4H18492P2 |
| | H4H18438P2 |
| H4H18438P2 | H4H18492P2 |
| | H4H18417P2 |
| H4H16650P2 | H4H16679P2 |
| H4H16679P2 | H4H16650P2 |
| H4H18445P2 | H4H18482P2 |
| | H4H18487P2 |
| | H4H18446P2 |
| H4H18446P2 | H4H18482P2 |
| | H4H18487P2 |
| | H4H18445P2 |
| H4H18482P2 | H4H18445P2 |
| | H4H18487P2 |
| H4H18487P2 | H4H18445P2 |
| | H4H18482P2 |
| H4H18449P2 | None |
| Comparator Antibody | None |

TABLE 15

| Cross-competition between anti-LEPR monoclonal antibodies | |
|---|---|
| mAb-1 | mAb-2 that competes with mAb-1 |
| H4H17319P2 | H4H17321P2 |
| | H4H16650P2 |
| | H4H16679P2 |
| H4H17321P2 | H4H17319P2 |
| | H4H16650P2 |
| | H4H16679P2 |
| H4H16650P2 | H4H17319P2 |
| | H4H17321P2 |
| | H4H16679P2 |
| H4H16679P2 | H4H17319P2 |
| | H4H17321P2 |
| | H4H16650P2 |

Example 10: In Vivo Efficacy of LEPR Agonist Antibodies H4H16650P2, H4H16679P2, H4H17319P2 and H4H17321P2 in an Inducible Mouse Model of Leptin Deficiency The effects of four specific agonist anti-LEPR antibodies of the invention, H4H16650P2, H4H16679P2, H4H17319P2, and H4H17321P2 on food intake, body weight and adiposity were determined in an inducible model of leptin deficiency in genetically engineered LEPR$^{Hu/Hu}$ mice, that express a leptin receptor which is composed of the human LEPR ectodomain sequence in place of the murine LEPR ectodomain sequence. The model of leptin deficiency was induced by hydrodynamic DNA delivery (HDD) of a plasmid encoding an hFc-tagged mouse LEPR ectodomain (referred to herein as mLEPR.hFc or "Leptin trap"; SEQ ID NO: 120). The Leptin trap when expressed is secreted and binds circulating Leptin. After HDD of 50 μg of the DNA construct encoding the Leptin trap, mice exhibited increased food consumption and increased adiposity and body weight.

Figure 3:
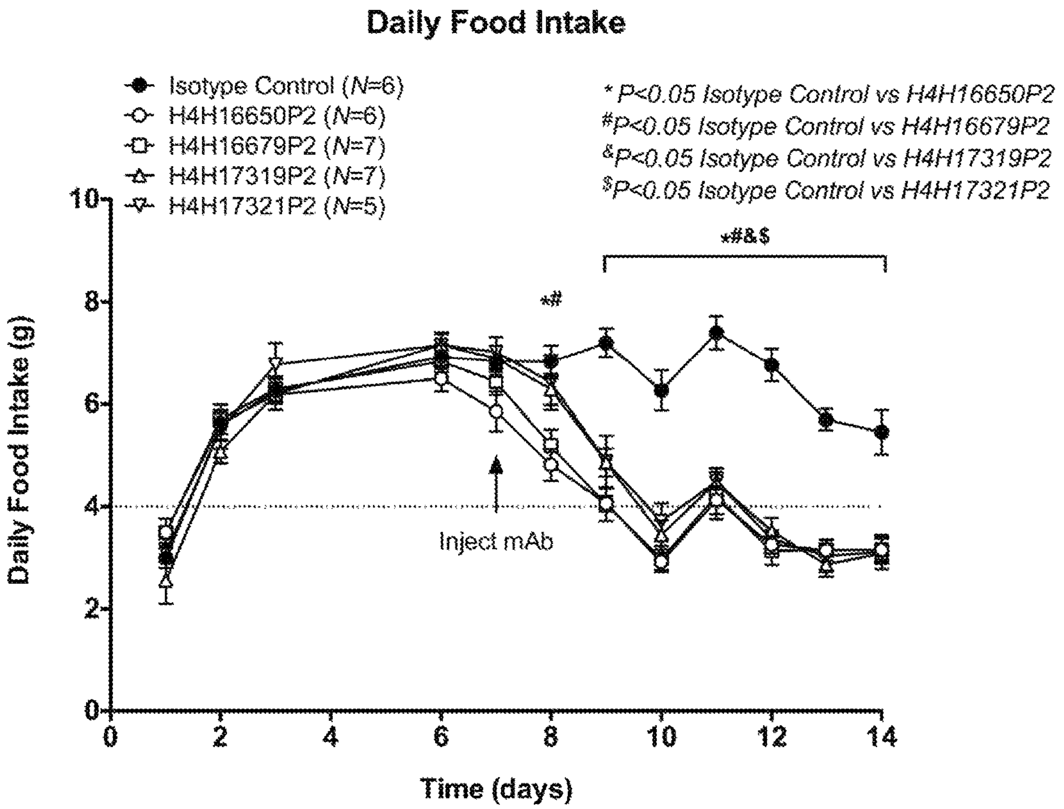
FIG. 3 shows the average daily food intake of leptin-deficient mice dosed with either an isotype control antibody at 3 mg/kg, or a LEPR antibody selected from H4H16650P2, H4H16679P2, H4H17319P2 or H4H17321P2 at 3 mg/kg.
Figure 4:
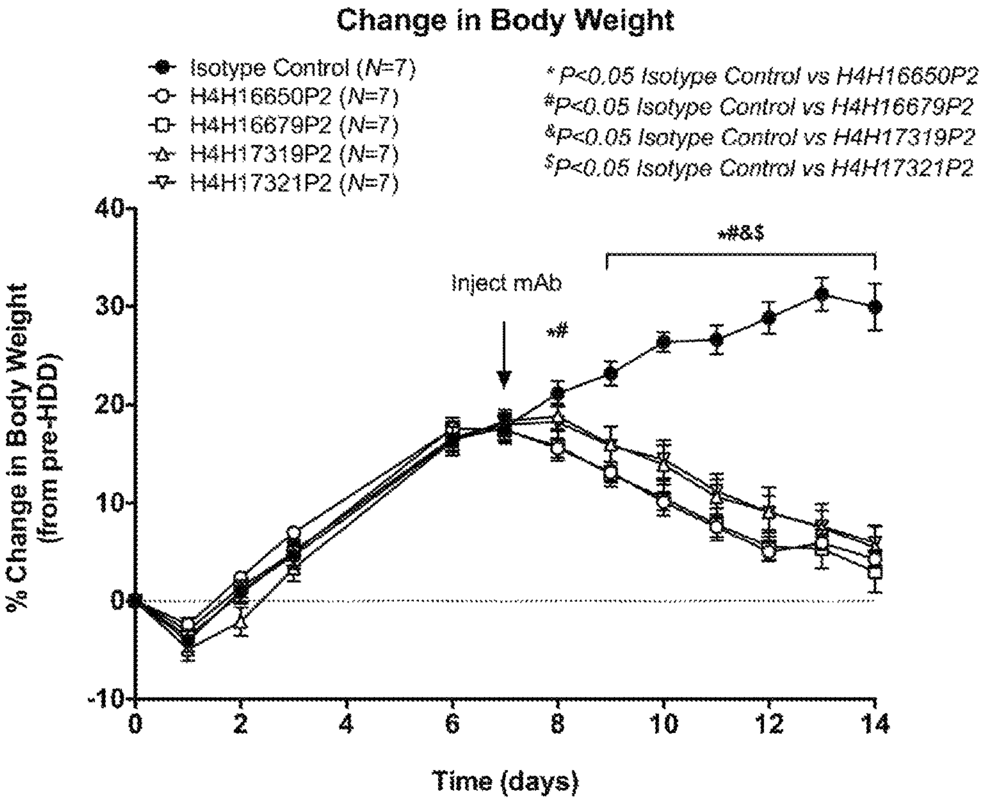
FIG. 4 shows the average percent change in body weight of mice dosed with either an isotype control antibody at 3 mg/kg, or a LEPR antibody selected from H4H16650P2, H4H16679P2, H4H17319P2 or H4H17321P2 at 3 mg/kg.
Figure 5:
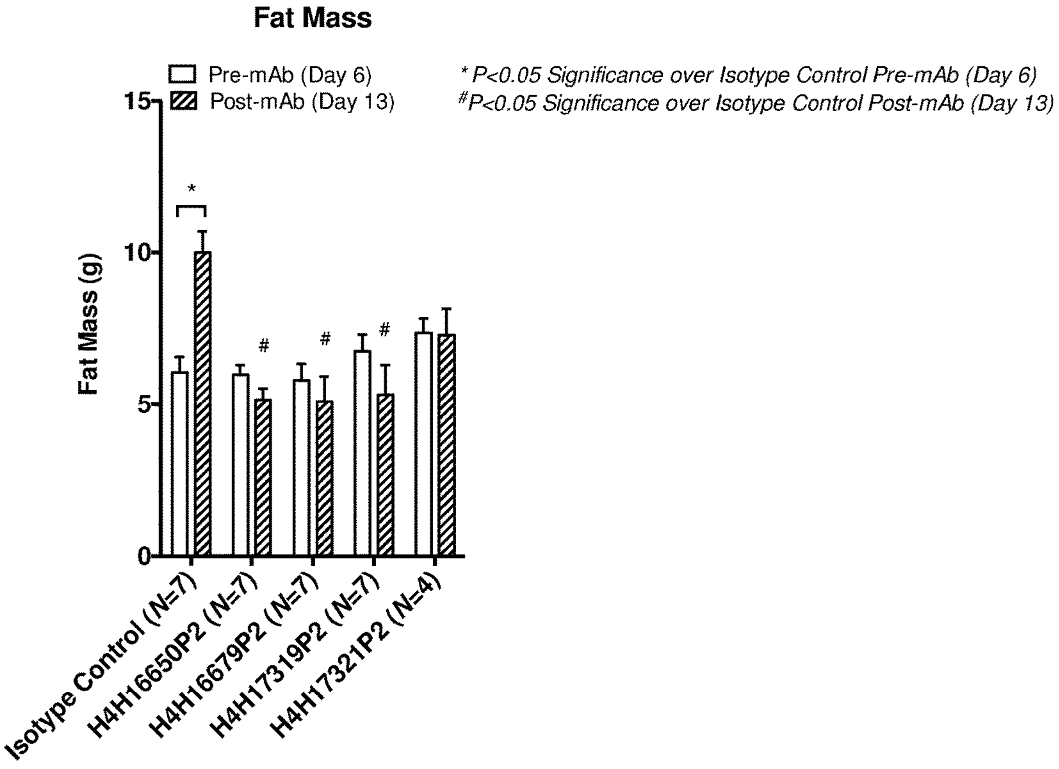
FIG. 5 shows the average fat mass for animals in each antibody treatment group quantified by μCT 1 day prior to (bars not shaded) and 6 days following antibody treatment (shaded bars) expressed as mean±SEM.

Baseline daily food intake was measured between 7 and 4 days prior to administration of the Leptin trap (days −7 and −4). On day 0, thirty-five 13- to 17-week old male LEPR$^{Hu/Hu}$ mice were successfully subjected to HDD with the Leptin trap. On days 6 and 13 post HDD, retro-orbital bleeds were collected and body composition including adiposity was quantified by μCT. On day 7 post HDD, mice were randomized into five groups of 7 mice based on percent body weight change from day 0. Each group received via subcutaneous injection either a single dose of isotype control antibody at 3 mg/kg, H4H16650P2 at 3 mg/kg, H4H16679P2 at 3 mg/kg, H4H17319P2 at 3 mg/kg, or H4H17321 at 3 mg/kg. The isotype control antibody did not bind any known mouse protein. Food intake and body weight were measured for each animal for the duration of the study. FIG. 3 summarizes the average daily food intake for each treatment group. In FIG. 3, the dotted line represents the average baseline food intake prior to HDD injection. The percent change in body weight from day 0 was calculated for each animal at each time point. FIG. 4 summarizes the average percent change in body weight for animals in each antibody treatment group. FIG. 5 summarizes the average fat mass for animals in each antibody treatment group quantified by μCT 1 day prior to and 6 days following antibody treatment. All results are expressed as mean±SEM.

As shown in FIGS. 3 and 4, following HDD with the Leptin trap, similar increases in food intake and percent change in body weight were observed among the groups of mice before antibody treatment. As shown in FIG. 3, mice treated with antibodies H4H16650P2 or H4H16679P2 at 3 mg/kg exhibited significant reductions in food intake starting at one day after antibody treatment (day 8 post HDD) and at subsequent time points measured as compared to mice injected with the isotype control antibody. Mice treated with antibodies H4H17319P2 or H4H17321P2 at 3 mg/kg exhibited a significant reduction in food intake at two days post antibody treatment (day 9 post HDD) and at the other subsequent time points measured as compared to mice injected with isotype control antibody. As shown in FIG. 4, mice treated with antibody H4H16650P2 at 3 mg/kg exhibited a significant reduction in percent body weight change one day after antibody treatment (day 8 post HDD) and at other subsequent time points measured as compared to mice injected with isotype control antibody. One day after antibody treatment, on day 8, mice treated with the isotype control showed a 21.16±1.27% increase in body weight from day 0, whereas mice treated with H4H16650P2 had a 15.57±0.9% increase in body weight from day 0. Mice treated with antibodies H4H16679P2, H4H17319P2 or H4H17321P2 at 3 mg/kg exhibited a significant reduction in percent body weight change two days after antibody treatment (day 9 post HDD) and at other subsequent time points measured as compared to mice injected with isotype control antibody. On day 9, the % body weight changes from day 0 were 23.18±1.22, 13.17±1.05, 12.95±1.26, 15.98±1.78 and 15.83±2.01 for mice treated with isotype control, H4H16650P2, H4H16679P2, H4H17319P2, or H4H17321P2, respectively. As shown in FIG. 5, mice treated with isotype control antibody at 3 mg/kg demonstrated a significant increase in fat mass 6 days after antibody treatment (day 13 post HDD) as compared to 1 day prior to antibody treatment (day 6 post HDD). Mice treated with antibodies H4H16650P2, H4H16679P2, H4H17319P2, or H4H17321P2 at 3 mg/kg did not gain adipose mass after antibody treatment as compared to pre-antibody treatment. After 6 days of treatment (day 13 post HDD), mice treated with antibodies H4H16650P2, H4H16679P2 or H4H17319P2 at 3 mg/kg demonstrated significant decreases in fat mass as compared to mice treated with isotype control antibody at 3 mg/kg.

Example 11: Epitope Mapping of H4H16650P2 Binding to Human Leptin Receptor (hLEPR.mmh) by Hydrogen Deuterium Exchange Experiments were conducted to determine the amino acid residues of hLEPR.mmh (amino acids M1-D839 of SEQ ID NO: 114) with which H4H16650P2 interacts. For this purpose H/D exchange epitope mapping with mass spectrometry was carried out. A general description of the H/D exchange method is set forth in, e.g., Ehring (1999) Analytical Biochemistry 267(2):252-259; and Engen and Smith (2001) Anal. Chem. 73:256A-265A.

Experimental Procedure.

HDX-MS experiments were performed on an integrated Waters HDX/MS platform, consisting of a Leaptec HDX PAL system for the deuterium labeling, a Waters Acquity M-Class (Auxiliary solvent manager) for the sample digestion and loading, a Waters Acquity M-Class (μ Binary solvent manager) for the analytical column gradient, and Synapt G2-Si mass spectrometer for peptic peptide mass measurement.

The labeling solution was prepared in 10 mM PBS buffer in D2O at pD 7.0 (equivalent to pH 6.6). For deterium labeling, 3.8 μL of hLEPR.mmh (8 pmol/μL) or hLEPR.mmh premixed with the antibody in 2:1 molar ratio was incubated with 56.2 μL D2O labeling solution for various time-points (e.g., undeuterated control=0 sec, labeled for 1 min and 20 min). The deuteration was quenched by transferring 50 μL sample to 50 μL pre-chilled quench buffer (0.2 M TCEP, 6 M guanidine chloride in 100 mM phosphate buffer, pH 2.5) and the mixed sample was incubated at 1.0° C. for two minutes. The quenched sample was then injected into a Waters HDX Manager for online pepsin/protease XIII digestion. The digested peptides were trapped onto an ACQUITY UPLC BEH C18 1.7-μm, 2.1×5 mm VanGuard pre-column at 0° C. and eluted to an analytical column ACQUITY UPLC BEH C18 1.7-μm, 1.0×50 mm for a 9-minute gradient separation of 5%-40% B (mobile phase A: 0.1% formic acid in water, mobile phase B: 0.1% formic acid in acetonitrile). The mass spectrometer was set at cone voltage of 37 V, scan time of 0.5 s, and mass/charge range of 50-1700 Th.

For the identification of the peptides from human LEPR, LC-MSE data from undeuterated sample were processed and searched against the database including human LEPR, pepsin, and their randomized sequences via Waters ProteinLynx Global Server (PLGS) software. The identified peptides were imported to DynamX software and filtered by two criteria: 1) minimum products per amino acid: 0.2, and 2) replication file threshold: 3. DynamX software then automatically determined deuterium uptake of each peptide based on retention time and high mass accuracy (<10 ppm) across multiple time points with 3 replicates at each time.

Results.

Using the online pepsin/protease XIII column coupled with $MS^E$ data acquisition, total 201 peptides from human LEPR were reproducibly identified in the absence or presence of the antibody, representing 70% sequence coverage. Five peptides had significantly reduced deuteration uptake (centroid delta values>0.4 daltons with p-values<0.05) when bound to H4H16650P2 as shown in the Table 16. The recorded peptide mass corresponds to the average value of the centroid $MH_+$ mass from three replicates. These peptides, corresponding to amino acids 162-169 (amino acids LYVLPEVL of human LEPR; SEQ ID NO: 113), and to amino acids 170-181 (amino acids EDSPLVPQKGSF of human LEPR; SEQ ID NO: 113), had a slower deuteration rate when bound to H4H16650P2. These identified residues also correspond to residues acids 162-169 and 170-181 of human LEPR as defined by Uniprot entry P48357 (SEQ ID NO. 113; Human leptin receptor)

TABLE 16

Human Leptin receptor peptides with significant protection upon binding to antibody H4H16650P2

| | 1 min Deuteration | | | 20 min Deuteration | | |
|---|---|---|---|---|---|---|
| Residues | hLEPR.mmh | hLEPR.mmh + H4H16650P2 | Δ | hLEPR.mmh | hLEPR.mmh + H4H16650P2 | Δ |
| 162-169 | 949.03 ± 0.03 | 947.99 ± 0.02 | −1.04 | 949.23 ± 0.02 | 948.16 ± 0.02 | −1.03 |
| 163-169 | 835.82 ± 0.03 | 834.79 ± 0.02 | −1.03 | 836.03 ± 0.02 | 834.94 ± 0.02 | −1.08 |
| 170-181 | 1310.02 ± 0.05 | 1309.12 ± 0.03 | −0.89 | 1309.77 ± 0.02 | 1309.38 ± 0.02 | −0.39 |

Example 12: In Vivo Efficacy Testing of LEPR Potentiator Antibodies in Humanized LEPR Mice The effects of three specific potentiator anti-LEPR antibodies of the invention, H4H18482P2, H4H18487P2 and H4H18492P2, on body weight and adiposity were determined in singly-housed genetically engineered $LEPR^{Hu/Hu}$ mice, that express a leptin receptor which is composed of the human LEPR ectodomain sequence in place of the murine LEPR ectodomain sequence (mLEPR.hFc, SEQ ID NO: 120).

Figure 6:
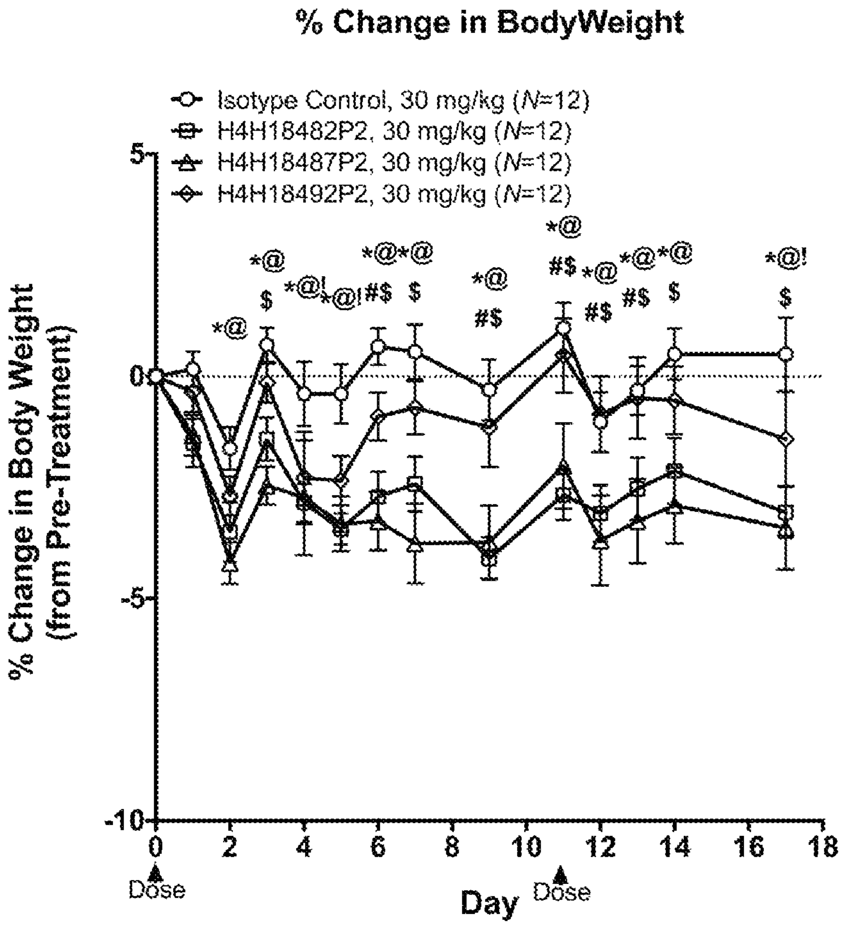
FIG. 6 shows the percent change in body weight of mice fed 30 mg/kg of an antibody selected from H4H18482P2, H4H18487P2, H4H18492P2 or an isotype control.

On days −19 body composition including adiposity was quantified by μCT. On days 0, forty-eight 14 to 16-week old female $LEPR^{Hu/Hu}$ mice were randomized to four groups of 12 mice based on body weight. On days 0 and 11, mice from each group received via subcutaneous injection a single dose of isotype control antibody at 30 mg/kg, H4H18482P2 at 30 mg/kg, H4H18487P2 at 30 mg/kg or H4H18492P2 at 30 mg/kg. The isotype control antibody does not bind any known mouse protein. Body weight was measured for the duration of the study for each animal. The percent change in body weight from day 0 was calculated for each animal at each time point. FIG. 6 summarizes the average percent change in body weight for animals in each treatment group. FIG. 6 summarizes the average fat mass for animals in each antibody treatment group quantified by μCT 19 days prior to and 11 days following antibody treatment. All results are expressed as mean±SEM.

As shown in FIG. 6, decreases in percent change in body weight were observed following dosing with the LEPR potentiator antibodies, but not the isotype control antibody.

As shown in FIG. 6, mice treated with H4H18482P2 at 30 mg/kg exhibited significant decreases in percent body weight change starting two days after treatment (day 2), and at the other time points compared to mice injected with an isotype control antibody. Mice treated with H4H18487P2 at 30 mg/kg exhibited significant decreases in percent body weight change starting at day 2 and at the other time points compared to mice injected with isotype control antibody. Mice treated with H4H18492P2 at 30 mg/kg exhibited a significant reduction in percent body weight change on days 4, 5 and 17 but not at other time points compared to mice injected with isotype control antibody. Mice treated with H4H18482P2 at 30 mg/kg exhibited a significant decrease in percent body weight change starting at day 6 and on subsequent days but not days 7, 14 and 17, compared to mice injected with H4H18492P2. Mice treated with H4H18487P2 at 30 mg/kg exhibited a significant decrease in percent body weight change starting at day 3 and at the other time points, but not days 4 and 5, compared to mice injected with H4H18492P2.

Figure 7A:
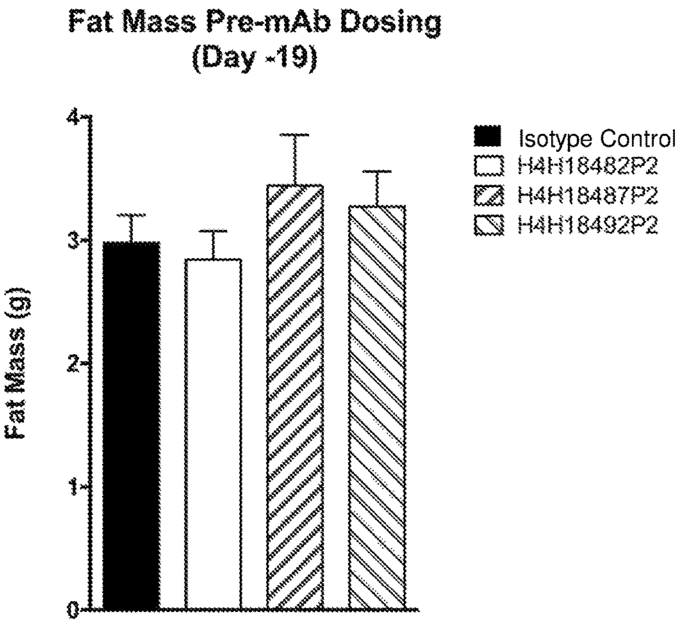
FIGS. 7A-7B.
Figure 7B:
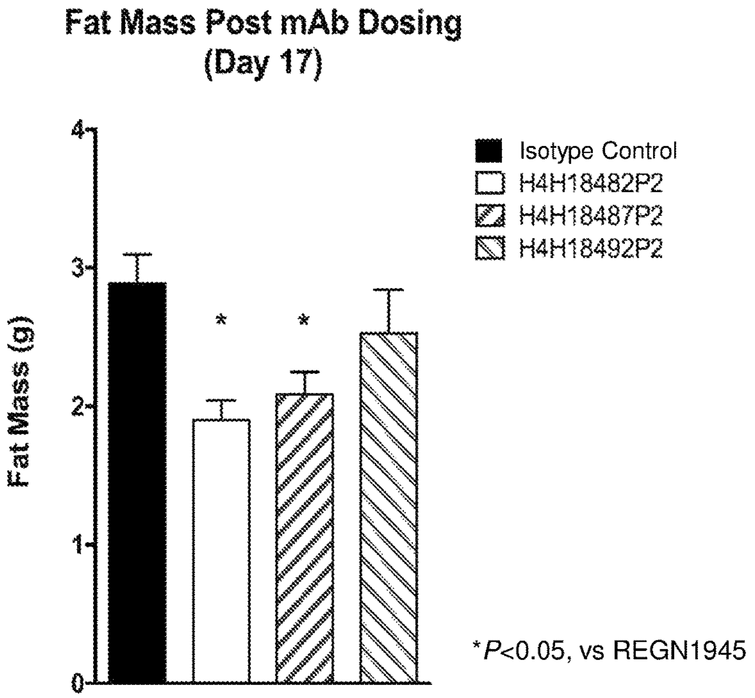
Figure 8:
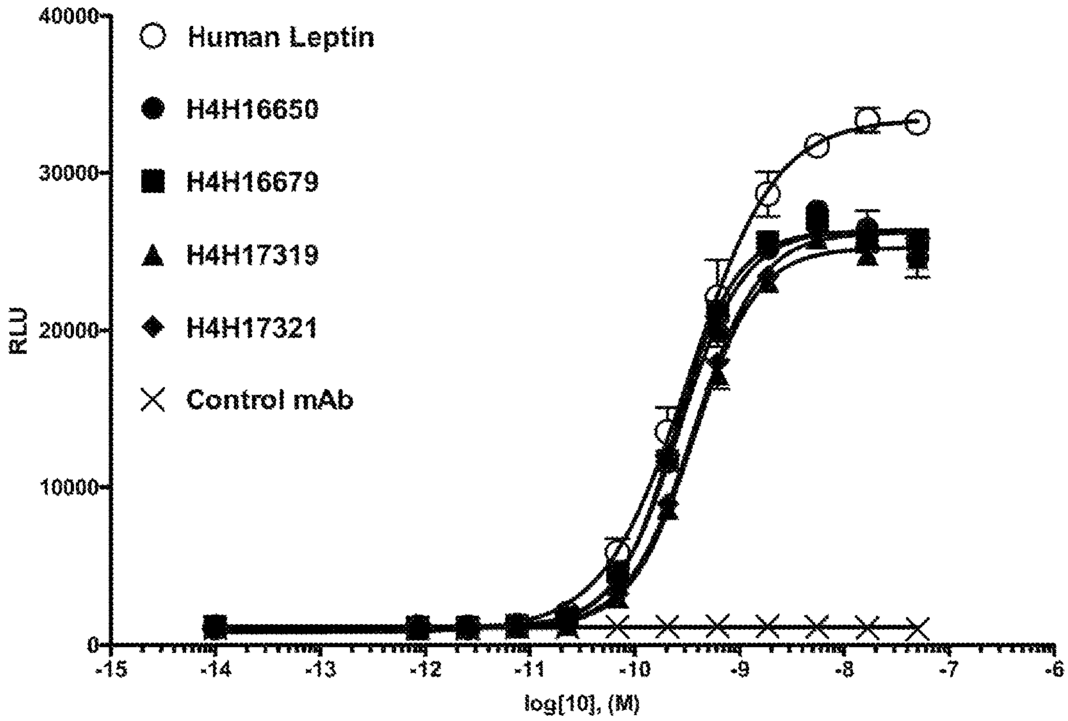
FIG. 8.

As shown in FIG. 7A, there were no differences in fat mass between the groups prior to treatment (day −19). As shown in FIG. 7B, mice treated with antibodies H4H18482 and H4H18487, but not H4H18492, at 30 mg/kg showed a statistically significant decrease in fat mass 17 days after treatment (day 12) as compared to the isotype control antibody.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Example 13: Effect of Anti-LEPR Antibodies of the Invention on Monkey LEPR Signaling In order to assess transcriptional activation of monkey Leptin receptor, a stable cell line was developed. IMR-32 cells (human Neuroblastoma ATCC) were generated to stably express the extracellular domain of *Macaca fascicularis* LEPR (MfLEPR; amino acids 22 through 837 of accession number XP_005543194.1 with threonine at 827 changed to alanine) fused with the transmembrane and cytosolic domains of human LEPR (hLEPR; amino acids 840 through 1165 of accession number NP_002294.2) along with a luciferase reporter (STAT3-Luc; SABiosciences, # CLS-6028L). The resulting cell line, referred to hereafter as IMR-32/STAT3-Luc/MfLEPR was isolated and maintained in MEM-Earl medium supplemented with 10% FBS, NEAA, 1 ug/mL Puromycin, 100 ug/mL of Hygromycin B and Penicillin/Streptomycin/L-Glutamine.

The bioassay was performed to measure the effect of anti-LEPR antibodies of the invention on monkey LEPR signaling in the absence of Leptin. For the bioassay, IMR-32/STAT3-Luc/MfLEPR cells were plated at 10,000 cells/well in a 96-well plate in 0.1% FBS in Optimem with penicillin/streptomycin (assay buffer) and incubated overnight at 37° C. in 5% $CO_2$. The following day human leptin (hLeptin), anti-LEPR antibodies or an isotype control antibody were serially diluted from 50 nM to 0.8 pM in the assay buffer (plus a sample containing buffer alone without test molecule) and added to the cells. After 5.5 hours at 37° C. in 5% $CO_2$, luciferase activity was measured with OneGlo™ reagent (Promega, # E6031) and Victor™ X multilabel plate reader (Perkin Elmer). The results were analyzed using nonlinear regression (4-parameter logistics) with Prism™6 software (Graph Pad) to obtain $EC_{50}$ values. Percentage of activation of antibodies was calculated as the maximum range of RLU achieved by the antibody relative to that of maximum range of RLU achieved by hLeptin.

As shown in Table 17, in the absence of hLeptin, all of the anti-LEPR antibodies tested showed activation of monkey LEPR signaling in IMR-32/STAT3-Luc/mfLEPR cells with $EC_{50}$ values ranging from 266 pM to 368 pM and maximal activation ranging from 76% to 82% where 100% activation was obtained with hLeptin. hLeptin activated with an $EC_{50}$ value of 333 pM. The isotype control antibody did not demonstrate any measurable stimulation of the IMR-32/STAT3-Luc/mfLEPR cells.

TABLE 17

Activation of *Macaca fascicularis* LEPR by anti-LEPR antibodies

| Leptin or Antibody | $EC_{50}$ (M) | % Activation |
|---|---|---|
| Human Leptin | 3.33E−11 | 100 |
| H4H16650P2 | 2.66E−10 | 82 |
| H4H16679P2 | 2.49E−10 | 80 |
| H4H17319P2 | 3.65E−10 | 76 |
| H4H17321P2 | 3.68E−10 | 78 |
| Isotype control antibody | No Activation | No Activation |

Example 14: Epitope Binding to the Full-Length Extracellular Domain of Human LEPR Using Luminex MFI Signal To determine the epitope of human LEPR on which anti-LEPR antibodies of the invention bind, a Luminex FLEXMAP (FM3DD, LuminexCorp) flow cytometry based analysis was utilized to characterize the interaction of anti-LEPR antibodies with recombinant human LEPR protein domains. For the assay, approximately 3 million carboxylated Microplex$^R$ microspheres (Luminex, Cat# LC1000A), were washed, vortexed and sonicated in 0.1 M $NaPO_4$, pH 6.2 (activation buffer) and then centrifuged to remove the supernatant. The microspheres were resuspended in 120 μL of activation buffer and the carboxylate groups (—COOH) were activated by addition of 15 μL of 50 mg/mL of N-hydroxysuccinimide (NHS, Thermo Scientific, Cat#24500) followed by addition of 15 μL of 50 mg/mL of 1-ethyl-3-[3-dimethylaminopropyl]carbodiimide (EDC, ThermoScientific, Cat#22980) at 25° C. After 10 minutes, the pH of the reaction was reduced to 5.0 with the addition of 600 μL of 50 mM MES, pH 5 (coupling buffer), and the microspheres were vortexed, and centrifuged to remove supernatant. The activated beads were immediately mixed with 500 μL of 20 μg/mL monoclonal anti-myc antibodies with either a mouse IgG or a human IgG, in coupling buffer and incubated for two hours at 25° C. The coupling reaction was quenched by addition of 50 μL of 1M Tris-HCl, pH 8.0 and the microspheres were rapidly vortexed, centrifuged, and washed four times with 1 mL of DPBS, to remove uncoupled proteins and other reaction components.

The transiently expressed LEPR proteins, including human LEPR extracellular domain expressed with a C-terminal myc-myc hexahistidine tag (human LEPR-MMH, SEQ ID NO: 113), human LEPR CRH1 (D1) expressed with a C-terminal myc-myc hexahistidine tag (human LEPR CRH1 (D1)-MMH, amino acids 1-208 of SEQ ID NO: 113 with a myc-myc hexahistidine tag, amino acids 209-236), human LEPR CRH1 (D1,D2) domain expressed with a C-terminal myc-myc hexahistidine tag (human LEPR CRH1 (D1,D2)-MMH, amino acids 1-318 of SEQ ID NO: 113 with a myc-myc hexahistidine tag, amino acids 319-346), human LEPR CRH1-Ig (D1,D2,D3) domain expressed with a C-terminal myc-myc hexahistidine tag (human LEPR CRH1 (D1,D2,D3)-MMH, amino acids 1-278 of SEQ ID NO: 113 with a myc-myc hexahistidine tag, amino acids 279-306), human LEPR CRH1-Ig (D2,D3) domain expressed with a C-terminal myc-myc hexahistidine tag (human LEPR CRH1-Ig (D2,D3)-MMH, amino acids 1-198 of SEQ ID NO: 113 with a myc-myc hexahistidine tag, amino acids 199-226), human LEPR Ig (D3) domain expressed with a C-terminal myc-myc hexahistidine tag (human LEPR Ig (D3)-MMH, amino acids 1-88 of SEQ iD NO: 113 with a myc-myc hexahistidine tag, amino acids 89-116), human LEPR CRH2 domain expressed with a C-terminal myc-myc hexahistidine tag (human LEPR CRH2-MMH, amino acids 1-207 of SEQ ID NO: 113 with a myc-myc-hexahistidine tag, amino acids 208-235), human LEPR FNIII domain expressed with a C-terminal myc-myc hexahistidine tag (human LEPR FNIII-MMH, amino acids 1-204 of SEQ ID NO: 113 with a myc-myc hexahistidine tage, amino acids 205-232), and human LEPR Ig-CRH2-FNIII domain expressed with a C-terminal myc-myc hexahistidine tag (human LEPR Ig-CRH2-FNIII-MMH, amino acids 1-510 of SEQ ID NO: 113 with a myc-myc-hexahistidine tag, amino acids 511-538), were suspended in serum free CHO-S-SFM II Medium (Thermo Fisher, Cat #31033020) and were then clarified by centrifugation. Aliquots of microspheres with immobilized anti-myc monoclonal antibodies, prepared as described above, were added individually to 1 mL of the each of these protein supernatants. The microspheres were gently mixed, incubated for two hours at 25° C., washed twice with 1 mL of DBPS, centrifuged to remove the supernatant and finally resuspended in 1 mL of DPBS buffer. Forty-eight μL of anti-myc IgG coupled microspheres from individual reactions with full length human LEPR and with each of the human LEPR domain proteins were withdrawn and mixed together in 3.6 mL of PBS+20 mg/mL BSA+ 0.05% sodium azide (blocking buffer).

From this mixed pool, 75 μL of microspheres were plated per well on a 96 well filter plate (Millipore, Cat. No: MSBVN1250) and mixed with 25 μL of individual anti-human LEPR monoclonal antibodies (0.5 or 5 μg/mL), incubated for two hours at 25° C. and then washed twice with 200 μL of DPBS with 0.05% Tween 20 (washing buffer). To detect and quantify the amounts of bound anti-LEPR antibody levels to individual microspheres, either 100 μL of 2.5 μg/mL R-Phycoerythrin conjugated goat F(ab')2 anti-human kappa (Southern Biotech, Cat#2063-09) in blocking buffer or 100 μL of 1.25 μg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer, was added and incubated for 30 minutes at 25° C. After 30 minutes, the samples were washed twice with 200 μL of washing buffer and resuspended in 150 μL of wash buffer. The Median Fluorescence intensity (MFI) of the microspheres was measured in a Luminex Analyzer.

TABLE 18

Luminex MFI signal of anti-LEPR antibodies binding to myc tag captured full-length extracellular domain of human LEPR and isonalted human LEPR domains

| Antibody | CRH1 (D1) | CRH1 (D1, D2) | CRH1-Ig (D1, D2, D3) | CRH1-Ig (D2, D3) | Ig (D3) | CRH2 | FNIII | Ig-CRH2-FNIII | Full Length extracellular domain | Probable Binding site |
|---|---|---|---|---|---|---|---|---|---|---|
| H4H18445P2 | 12 | 30 | 22 | 40 | 19 | 17 | 230 | 14544 | 6573 | FNIII |
| H4H18446P2 | 17 | 682 | 205 | 645 | 25 | 65 | 32 | 16852 | 10536 | Ig-CRH2-FNIII |
| H4H18482P2 | 13 | 40 | 21 | 52 | 27 | 23 | 167 | 15316 | 7311 | Ig-CRH2-FNIII |
| H4H18487P2 | 12 | 51 | 29 | 62 | 22 | 27 | 174 | 16320 | 7329 | Ig-CRH2-FNIII |
| H4H18417P2 | 10 | 16048 | 3334 | 5502 | 17 | 39 | 14 | 37 | 4887 | CRH1 D2 |
| H4H18438P2 | 13 | 18931 | 6572 | 8884 | 30 | 165 | 25 | 468 | 6251 | CRH1 D2 |
| H4H18492P2 | 11 | 19371 | 6354 | 8685 | 19 | 18 | 16 | 186 | 6382 | CRH1 D2 |
| H4H18449P2 | 20 | 2934 | 2056 | 42 | 24 | 15 | 13 | 43 | 7976 | CRH1(D1-2) |
| H4H16650P2 | 8 | 4722 | 2562 | 74 | 10 | 16 | 6 | 110 | 7603 | CRH1(D1-2) |
| H4H16679P2 | 12 | 4388 | 2797 | 34 | 14 | 33 | 10 | 42 | 7507 | CRH1(D1-2) |
| H4H17319P2 | 8 | 1246 | 938 | 14 | 8 | 91 | 20 | 8 | 3305 | CRH1(D1-2) |
| H4H17321P2 | 9 | 2649 | 1752 | 15 | 7 | 116 | 40 | 14 | 4696 | CRH1(D1-2) |
| Comparator mAb | −14 | 19 | −57 | 27 | 10 | 9404 | 73 | 7112 | 3908 | CRH2 |

The results of the Luminex based analysis are tabulated in Table 18. Luminex MFI signal intensities indicate that the twelve anti-LEPR antibodies of the invention bound to the complete human LEPR extracellular domain. Anti-LEPR antibodies H4H18417P2, H4H18438P2, and H4H18492P2, bound to epitopes within the CRH1 D2 domain of human LEPR. Anti-LEPR antibodies H4H18449P2, H4H16650P and H4H16679P, bound to epitopes within the CRH1(D1-2) domain of human LEPR. Anti-LEPR antibody Comparator mAB, bound to epitopes within the CRH2 domain of human LEPR. Anti-LEPR antibody H4H18445P2 bound to epitopes within the FNIII domain of human LEPR. Anti-LEPR antibodies H4H18446P2, H4H18482P2 and H4H18487P2, bound to epitopes within the Ig-CRH2-FNIII domain of human LEPR.

What is claimed is:

1. An isolated antibody or antigen-binding fragment thereof that binds human leptin receptor (LEPR) which comprises:

the light chain complementarity determining regions (CDRs) of a light chain variable region that comprises the amino acid sequence set forth in SEQ ID NO: 10; and the heavy chain CDRs of a heavy chain variable region that comprises the amino acid sequence set forth in SEQ ID NO: 2, SEQ ID NO: 26 or SEQ ID NO: 34.

2. An isolated antibody or antigen-binding fragment thereof that binds human leptin receptor (LEPR) which comprises:

a light chain variable region that comprises the amino acid sequence set forth in SEQ ID NO: 10; and a heavy chain variable region that comprises the amino acid sequence set forth in SEQ ID NO: 2, SEQ ID NO: 26 or SEQ ID NO: 34.

3. An isolated antibody or antigen-binding fragment thereof that binds human leptin receptor (LEPR) which comprises a light chain variable region that comprises the amino acid sequence set forth in SEQ ID NO: 10; and a heavy chain variable region that comprises the amino acid sequence set forth in SEQ ID NO: 2.

4. The antibody or antigen-binding fragment of claim 3 which is an antibody.

5. The antibody of claim 4 wherein the heavy chain variable region is linked to a human IgG1 heavy chain constant domain and the light chain variable region is linked to a human kappa light chain constant domain.

6. The antibody of claim 4 wherein the heavy chain variable region is linked to a human IgG4 heavy chain constant domain and the light chain variable region is linked to a human kappa light chain constant domain.

7. An isolated antibody or antigen-binding fragment thereof that binds human leptin receptor (LEPR) which comprises a light chain variable region that comprises the amino acid sequence set forth in SEQ ID NO: 10; and a heavy chain variable region that comprises the amino acid sequence set forth in SEQ ID NO: 26.

8. The antibody or antigen-binding fragment of claim 7 which is an antibody.

9. The antibody of claim 8 which wherein the heavy chain variable region is linked to a human IgG1 heavy chain constant domain and the light chain variable region is linked to a human kappa light chain constant domain.

10. The antibody of claim 8 which wherein the heavy chain variable region is linked to a human IgG4 heavy chain constant domain and the light chain variable region is linked to a human kappa light chain constant domain.

11. An isolated antibody or antigen-binding fragment thereof that binds human leptin receptor (LEPR) which comprises a light chain variable region that comprises the amino acid sequence set forth in SEQ ID NO: 10; and a heavy chain variable region that comprises the amino acid sequence set forth in SEQ ID NO: 34.

12. The antibody or antigen-binding fragment of claim 11 which is an antibody.

13. The antibody of claim 12 which wherein the heavy chain variable region is linked to a human IgG1 heavy chain constant domain and the light chain variable region is linked to a human kappa light chain constant domain.

14. The antibody of claim 12 which wherein the heavy chain variable region is linked to a human IgG4 heavy chain constant domain and the light chain variable region is linked to a human kappa light chain constant domain.

15. A pharmaceutical composition comprising the antibody of claim 4 and a pharmaceutically acceptable carrier or diluent.

16. A pharmaceutical composition comprising the antibody of claim 8 and a pharmaceutically acceptable carrier or diluent.

17. A pharmaceutical composition comprising the antibody of claim 12 and a pharmaceutically acceptable carrier or diluent.

18. The antibody of claim 4 in combination with one or more additional therapeutically active components.

19. The antibody of claim 8 in combination with one or more additional therapeutically active components.

20. The antibody of claim 12 in combination with one or more additional therapeutically active components.

21. A pen delivery device comprising the pharmaceutical composition of claim 15.

22. A pen delivery device comprising the pharmaceutical composition of claim 16.

23. A pen delivery device comprising the pharmaceutical composition of claim 17.

24. The antibody of claim 4 in combination with recombinant human leptin, alirocumab, evolocumab, bococizumab, lodelcizumab, ralpancizumab, atorvastatin, rosuvastatin, cerivastatin, pitavastatin, fluvastatin, simvastatin, lovastatin, pravastatin, ezetimibe, insulin, metformin, dapaglifozin, canaglifozin, empagliflozin, extendin-4, exenatide, liraglutide, lixisenatide, albiglutide, dulaglutide, an anti-GCG antibody, an anti-GCGR antibody, an anti-ANGPTL3 antibody, an anti-ANGPTL4 antibody, anti-ANGPTL8 antibody, phentermine, orlistat, topiramate, bupropion, topiramate and phentermine, bupropion and naltrexone, bupropion and zonisamide, pramlintide and metrelepin, lorcaserin, cetilistat, tesofensine or velneperit.

25. The antibody of claim 8 in combination with recombinant human leptin, alirocumab, evolocumab, bococizumab, lodelcizumab, ralpancizumab, atorvastatin, rosuvastatin, cerivastatin, pitavastatin, fluvastatin, simvastatin, lovastatin, pravastatin, ezetimibe, insulin, metformin, dapaglifozin, canaglifozin, empagliflozin, extendin-4, exenatide, liraglutide, lixisenatide, albiglutide, dulaglutide, an anti-GCG antibody, an anti-GCGR antibody, an anti-ANGPTL3 antibody, an anti-ANGPTL4 antibody, anti-ANGPTL8 antibody, phentermine, orlistat, topiramate, bupropion, topiramate and phentermine, bupropion and naltrexone, bupropion and zonisamide, pramlintide and metrelepin, lorcaserin, cetilistat, tesofensine or velneperit.

26. The antibody of claim 12 in combination with recombinant human leptin, alirocumab, evolocumab, bococizumab, lodelcizumab, ralpancizumab, atorvastatin, rosuvastatin, cerivastatin, pitavastatin, fluvastatin, simvastatin, lovastatin, pravastatin, ezetimibe, insulin, metformin, dapaglifozin, canaglifozin, empagliflozin, extendin-4, exenatide, liraglutide, lixisenatide, albiglutide, dulaglutide, an anti-GCG antibody, an anti-GCGR antibody, an anti-ANGPTL3 antibody, an anti-ANGPTL4 antibody, anti-ANGPTL8 antibody, phentermine, orlistat, topiramate, bupropion, topiramate and phentermine, bupropion and naltrexone, bupropion and zonisamide, pramlintide and metrelepin, lorcaserin, cetilistat, tesofensine or velneperit.

27. The antibody of claim 4 which is bispecific.

28. The antibody of claim 8 which is bispecific.

29. The antibody of claim 12 which is bispecific.

* * * * *

SEQUENCE LISTING

<160> NUMBER OF SEQ ID NOS: 120

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1
caggtgcagc tggtggagtc tgggggaggc gtggtccagc ctgggaagtc cctgagactc 60
tcctgtgtag cgtctggatt caccttcagt tccgatgcca tgtactgggt ccgccaggct 120
ccaggcaagg ggctggaatg ggtggcagtt atttattatg atggaaatta tcaatactat 180
gaagactccg ttaagggtcg attcaccatc tccagagaca attcccagaa cacgctggat 240
ctgcaaatga acagcctgag agtcgacgac acggctgtat atttctgtgc gcgtctcaac 300
tgggattact ggtatctcga tctctggggc cgtggcaccc tggtcactgt ctcctca 357

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Lys
1 5 10 15

Ser Leu Arg Leu Ser Cys Val Ala Ser Gly Phe Thr Phe Ser Ser Asp
20 25 30

Ala Met Tyr Trp Val Arg Gln Ala Pro Gly Lys Gly Leu Glu Trp Val
35 40 45

Ala Val Ile Tyr Tyr Asp Gly Asn Tyr Gln Tyr Tyr Glu Asp Ser Val
50 55 60

Lys Gly Arg Phe Thr Ile Ser Arg Asp Asn Ser Gln Asn Thr Leu Asp
65 70 75 80

Leu Gln Met Asn Ser Leu Arg Val Asp Asp Thr Ala Val Tyr Phe Cys
85 90 95

Ala Arg Leu Asn Trp Asp Tyr Trp Tyr Leu Asp Leu Trp Gly Arg Gly
100 105 110

Thr Leu Val Thr Val Ser Ser
115

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagttccga tgcc 24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Asp Ala
1 5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atttattatg atggaaatta tcaa 24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Tyr Tyr Asp Gly Asn Tyr Gln
1 5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
gcgcgtctca actgggatta ctggtatctc gatctc 36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ala Arg Leu Asn Trp Asp Tyr Trp Tyr Leu Asp Leu
1 5 10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

```
Gln Ser Ile Ser Ser Tyr
1               5
```

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc 9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

```
Ala Ala Ser
1
```

-continued

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagagtt acagtacccc tccgatcacc 30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1 5 10

<210> SEQ ID NO 17
<211> LENGTH: 357
<212> TYPE: DNA
<213> ORGANISM: Artificial Sequence
<220> FEATURE:
<223> OTHER INFORMATION: synthetic

<400> SEQUENCE: 17
caggtgcagc tggtggagtc cgggggaggc gtggtccagc ctgggaggtc cctgagactc 60
tcctgtacag cgtctggatt caccttcagt agttatgcca tgtactgggt ccgccaggct 120
ccaggcaagg ggctggagtg ggtgtcagtt atatactatg atggaagtta taaatactat 180
gcagactccg tgaagggccg attcaccatc tccagagaca attccaagaa cacgctgtat 240
ctgcaaatgg acagcctgag agccgaggac acggctgtct attactgtgc gagttataac 300
tggaactact ggtacttcga tttctggggc cgtggcaccc tggtcactgt ctcctca 357

<210> SEQ ID NO 18
<211> LENGTH: 119
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Val Val Gln Pro Gly Arg
1 5 10 15

Ser Leu Arg Leu Ser Cys Thr Ala Ser Gly Phe Thr Phe Ser Ser Tyr
20 25 30

Ala Met Tyr Trp Val Arg Gln Ala Pro Gly Lys Gly Leu Glu Trp Val
35 40 45

Ser Val Ile Tyr Tyr Asp Gly Ser Tyr Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asp Ser Leu Arg Ala Glu Asp Thr Ala Val Tyr Tyr Cys
85 90 95

Ala Ser Tyr Asn Trp Asn Tyr Trp Tyr Phe Asp Phe Trp Gly Arg Gly
100 105 110

Thr Leu Val Thr Val Ser Ser
115

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtagtta tgcc 24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Ala
1 5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
atatactatg atggaagtta taaa 24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Tyr Tyr Asp Gly Ser Tyr Lys
1 5

<210> SEQ ID NO 23
<211> LENGTH: 36
<212> TYPE: DNA
<213> ORGANISM: Artificial Sequence
<220> FEATURE:
<223> OTHER INFORMATION: synthetic

<400> SEQUENCE: 23
gcgagttata actggaacta ctggtacttc gatttc 36

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Ser Tyr Asn Trp Asn Tyr Trp Tyr Phe Asp Phe
1 5 10

<210> SEQ ID NO 25
<211> LENGTH: 357
<212> TYPE: DNA
<213> ORGANISM: Artificial Sequence -continued
<220> FEATURE:
<223> OTHER INFORMATION: synthetic

<400> SEQUENCE: 25
caggtgcagc tggtggagtc tgggggaagc gtggtccagc ctgggaggtc cctgagactc 60
tcctgtgcag cgtctggatt caccttcagt acatatgcca tgtactgggt ccgccagact 120
ccaggcaagg ggctggagtg ggtggctgtt ttatactctg atggaagtaa taaatactat 180
atagactccg tgaagggccg attcaccatc tccagagaca cttccacgaa cactctgtat 240
ctgcaaatga gcagcctgcg agccgacgac tcggctctat attactgtgc gcgtctcaac 300
tgggattact ggtacttcga tctctggggc cgtggcaccc tggtcactgt ctcctca 357

<210> SEQ ID NO 26
<211> LENGTH: 119
<212> TYPE: PRT
<213> ORGANISM: Artificial Sequence
<220> FEATURE:
<223> OTHER INFORMATION: synthetic

<400> SEQUENCE: 26

Gln Val Gln Leu Val Glu Ser Gly Gly Ser Val Val Gln Pro Gly Arg
1 5 10 15

Ser Leu Arg Leu Ser Cys Ala Ala Ser Gly Phe Thr Phe Ser Thr Tyr
20 25 30

Ala Met Tyr Trp Val Arg Gln Thr Pro Gly Lys Gly Leu Glu Trp Val
35 40 45

Ala Val Leu Tyr Ser Asp Gly Ser Asn Lys Tyr Tyr Ile Asp Ser Val
50 55 60

Lys Gly Arg Phe Thr Ile Ser Arg Asp Thr Ser Thr Asn Thr Leu Tyr
65 70 75 80

Leu Gln Met Ser Ser Leu Arg Ala Asp Asp Ser Ala Leu Tyr Tyr Cys
85 90 95

Ala Arg Leu Asn Trp Asp Tyr Trp Tyr Phe Asp Leu Trp Gly Arg Gly
100 105 110

Thr Leu Val Thr Val Ser Ser
115

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ggattcacct tcagtacata tgcc 24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Ser Thr Tyr Ala
1 5

-continued

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
ttatactctg atggaagtaa taaa 24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Leu Tyr Ser Asp Gly Ser Asn Lys
1 5

<210> SEQ ID NO 31
<211> LENGTH: 36
<212> TYPE: DNA
<213> ORGANISM: Artificial Sequence
<220> FEATURE:
<223> OTHER INFORMATION: synthetic

<400> SEQUENCE: 31
gcgcgtctca actgggatta ctggtacttc gatctc 36

<210> SEQ ID NO 32
<211> LENGTH: 12
<212> TYPE: PRT
<213> ORGANISM: Artificial Sequence
<220> FEATURE:
<223> OTHER INFORMATION: synthetic

<400> SEQUENCE: 32

Ala Arg Leu Asn Trp Asp Tyr Trp Tyr Phe Asp Leu
1 5 10

<210> SEQ ID NO 33
<211> LENGTH: 357
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctgggaggtc cctgagactc 60
tcctgtgaag cgtctggatt cagcagcagt gacaatgcca tgtactgggt ccgccaggct 120
ccaggcaagg ggctggagtg ggtgtcagtt atatatcatg atggaagtta taaatactat 180
gaagactccg tgaagggccg attcaccatc gccagagaca attccaagaa cacgctttat 240
ttgcaaatga acagcctgag agccgaggac acggctgtat attactgtgc gaggtataac 300
tggaaccact ggtacttcga tgtctggggc cgtggcaccc tggtcactgt ctcctca 357

<210> SEQ ID NO 34
<211> LENGTH: 119
<212> TYPE: PRT
<213> ORGANISM: Artificial Sequence
<220> FEATURE:
<223> OTHER INFORMATION: synthetic

<400> SEQUENCE: 34

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Ser Ser Ser Asp Asn
            20                  25                  30

Ala Met Tyr Trp Val Arg Gln Ala Pro Gly Lys Gly Leu Glu Trp Val
        35                  40                  45

Ser Val Ile Tyr His Asp Gly Ser Tyr Lys Tyr Tyr Glu Asp Ser Val
    50                  55                  60

Lys Gly Arg Phe Thr Ile Ala Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Trp Asn His Trp Tyr Phe Asp Val Trp Gly Arg Gly
            100                 105                 110

Thr Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcagca gcagtgacaa tgcc 24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Ser Ser Ser Asp Asn Ala
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatatcatg atggaagtta taaa 24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Tyr His Asp Gly Ser Tyr Lys
1               5

<210> SEQ ID NO 39
<211> LENGTH: 36
<212> TYPE: DNA
<213> ORGANISM: Artificial Sequence
<220> FEATURE:
<223> OTHER INFORMATION: synthetic

<400> SEQUENCE: 39
gcgaggtata actggaacca ctggtacttc gatgtc 36

<210> SEQ ID NO 40
<211> LENGTH: 12
<212> TYPE: PRT
<213> ORGANISM: Artificial Sequence
<220> FEATURE:
<223> OTHER INFORMATION: synthetic

<400> SEQUENCE: 40

Ala Arg Tyr Asn Trp Asn His Trp Tyr Phe Asp Val
1 5 10

<210> SEQ ID NO 41
<211> LENGTH: 366
<212> TYPE: DNA
<213> ORGANISM: Artificial Sequence
<220> FEATURE:
<223> OTHER INFORMATION: synthetic

<400> SEQUENCE: 41
caggtgcagc tggtggagtc tgggggaggc gtggtccagc ctgggaggtc cctgagactc 60
tcctgtgcag cctctggatt caccttcagt acctatggca tgcactgggt ccgccaggct 120
ccaggcaagg ggctggagtg ggtgtcagtt atatcatatg acgaaagtaa taagtactat 180
gcagactccg tgaagggccg attcaccatt tctagagaca attccaagaa cgcgctgtat 240
ttacaaatga acagcctgag aaatgaggac acggctgtgt attactgtgc gagagatcgg 300
ccttttggat tggttaccgg atggttcgac ccctggggcc agggaaccct ggtcaccgtc 360
tcctca 366

<210> SEQ ID NO 42
<211> LENGTH: 122
<212> TYPE: PRT
<213> ORGANISM: Artificial Sequence
<220> FEATURE:
<223> OTHER INFORMATION: synthetic

<400> SEQUENCE: 42

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Thr Tyr
20 25 30

Gly Met His Trp Val Arg Gln Ala Pro Gly Lys Gly Leu Glu Trp Val
35 40 45

Ser Val Ile Ser Tyr Asp Glu Ser Asn Lys Tyr Tyr Ala Asp Ser Val
50 55 60

Lys Gly Arg Phe Thr Ile Ser Arg Asp Asn Ser Lys Asn Ala Leu Tyr
65 70 75 80

Leu Gln Met Asn Ser Leu Arg Asn Glu Asp Thr Ala Val Tyr Tyr Cys
85 90 95

-continued

Ala Arg Asp Arg Pro Phe Gly Leu Val Thr Gly Trp Phe Asp Pro Trp
100 105 110

Gly Gln Gly Thr Leu Val Thr Val Ser Ser
115 120

<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43
ggattcacct tcagtaccta tggc 24

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Ser Thr Tyr Gly
1 5

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
atatcatatg acgaaagtaa taag 24

<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Tyr Asp Glu Ser Asn Lys
1 5

<210> SEQ ID NO 47
<211> LENGTH: 45
<212> TYPE: DNA
<213> ORGANISM: Artificial Sequence
<220> FEATURE:
<223> OTHER INFORMATION: synthetic

<400> SEQUENCE: 47
gcgagagatc ggccttttgg attggttacc ggatggttcg acccc 45

<210> SEQ ID NO 48
<211> LENGTH: 15
<212> TYPE: PRT
<213> ORGANISM: Artificial Sequence
<220> FEATURE:
<223> OTHER INFORMATION: synthetic

<400> SEQUENCE: 48

Ala Arg Asp Arg Pro Phe Gly Leu Val Thr Gly Trp Phe Asp Pro
1 5 10 15

<210> SEQ ID NO 49
<211> LENGTH: 360
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc gtggtccagc ctgggaggtc cctgagactc 60
tcctgtgcag cgtctggatt cagtttcaat acctatggca tgcactgggt ccgccaggct 120
ccaggcaagg ggctggagtg ggtgacaatt atatggtatg atggaagtat taaatactat 180
gcagactccg tgaagggccg attcaccatc tccagagaca attccaagaa cacgctgtat 240
ctgcaaatga acagcctgag agccgaggac acggctgtgt attattgtgc gagaggtgga 300
tatagtggct acctctactt tgactactgg ggccagggaa ccctggtcac cgtctcctca 360

<210> SEQ ID NO 50
<211> LENGTH: 120
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Asn Thr Tyr
20 25 30

Gly Met His Trp Val Arg Gln Ala Pro Gly Lys Gly Leu Glu Trp Val
35 40 45

Thr Ile Ile Trp Tyr Asp Gly Ser Ile Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Tyr Ser Gly Tyr Leu Tyr Phe Asp Tyr Trp Gly Gln
100 105 110

Gly Thr Leu Val Thr Val Ser Ser
115 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcagtt tcaataccta tggc 24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Ser Phe Asn Thr Tyr Gly
1 5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatggtatg atggaagtat taaa 24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Trp Tyr Asp Gly Ser Ile Lys
1 5

<210> SEQ ID NO 55
<211> LENGTH: 39
<212> TYPE: DNA
<213> ORGANISM: Artificial Sequence
<220> FEATURE:
<223> OTHER INFORMATION: synthetic

<400> SEQUENCE: 55
gcgagaggtg gatatagtgg ctacctctac tttgactac 39

<210> SEQ ID NO 56
<211> LENGTH: 13
<212> TYPE: PRT
<213> ORGANISM: Artificial Sequence
<220> FEATURE:
<223> OTHER INFORMATION: synthetic

<400> SEQUENCE: 56

Ala Arg Gly Gly Tyr Ser Gly Tyr Leu Tyr Phe Asp Tyr
1 5 10

<210> SEQ ID NO 57
<211> LENGTH: 372
<212> TYPE: DNA
<213> ORGANISM: Artificial Sequence
<220> FEATURE:
<223> OTHER INFORMATION: synthetic

<400> SEQUENCE: 57
caggtgcagc tgcaggagtc gggcccagga ctggtgaagc cttcacagac cctgtccctc 60
acctgcactg tctctggtgg ctccatcagc agcggtggtg actactggag ctggatccgc 120
cagctcccag ggaagggcct ggagtggatt gggtacatct attacagtgg gagcgcctac 180
tataatccgt ccctcaagag tcgaggtacc atatcaatag acacgtctaa gaaccagttc 240
tccctgaagc tgacctctgt gactgccgcg gacacggccg tatatttctg tgtgaaatta 300

-continued cgatttttgg agtggttctt ggggggctgg ttcggcccct ggggccaggg aaccctggtc 360
accgtctcct ca 372

<210> SEQ ID NO 58
<211> LENGTH: 124
<212> TYPE: PRT
<213> ORGANISM: Artificial Sequence
<220> FEATURE:
<223> OTHER INFORMATION: synthetic

<400> SEQUENCE: 58

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Asp Tyr Trp Ser Trp Ile Arg Gln Leu Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60

Leu Lys Ser Arg Gly Thr Ile Ser Ile Asp Thr Ser Lys Asn Gln Phe
65                  70                  75                  80

Ser Leu Lys Leu Thr Ser Val Thr Ala Ala Asp Thr Ala Val Tyr Phe
                85                  90                  95

Cys Val Lys Leu Arg Phe Leu Glu Trp Phe Leu Gly Gly Trp Phe Gly
            100                 105                 110

Pro Trp Gly Gln Gly Thr Leu Val Thr Val Ser Ser
        115                 120
```

<210> SEQ ID NO 59
<211> LENGTH: 30
<212> TYPE: DNA
<213> ORGANISM: Artificial Sequence
<220> FEATURE:
<223> OTHER INFORMATION: synthetic

<400> SEQUENCE: 59
ggtggctcca tcagcagcgg tggtgactac 30

<210> SEQ ID NO 60
<211> LENGTH: 10
<212> TYPE: PRT
<213> ORGANISM: Artificial Sequence
<220> FEATURE:
<223> OTHER INFORMATION: synthetic

<400> SEQUENCE: 60

```
Gly Gly Ser Ile Ser Ser Gly Gly Asp Tyr
1               5                   10
```

<210> SEQ ID NO 61
<211> LENGTH: 21
<212> TYPE: DNA
<213> ORGANISM: Artificial Sequence
<220> FEATURE:
<223> OTHER INFORMATION: synthetic

<400> SEQUENCE: 61
atctattaca gtgggagcgc c 21

<210> SEQ ID NO 62
<211> LENGTH: 7
<212> TYPE: PRT
<213> ORGANISM: Artificial Sequence
<220> FEATURE:
<223> OTHER INFORMATION: synthetic

<400> SEQUENCE: 62

Ile Tyr Tyr Ser Gly Ser Ala
1 5

<210> SEQ ID NO 63
<211> LENGTH: 48
<212> TYPE: DNA
<213> ORGANISM: Artificial Sequence
<220> FEATURE:
<223> OTHER INFORMATION: synthetic

<400> SEQUENCE: 63
gtgaaattac gatttttgga gtggttcttg gggggctggt tcggcccc 48

<210> SEQ ID NO 64
<211> LENGTH: 16
<212> TYPE: PRT
<213> ORGANISM: Artificial Sequence
<220> FEATURE:
<223> OTHER INFORMATION: synthetic

<400> SEQUENCE: 64

Val Lys Leu Arg Phe Leu Glu Trp Phe Leu Gly Gly Trp Phe Gly Pro
1 5 10 15

<210> SEQ ID NO 65
<211> LENGTH: 351
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtacagc cggggggtc cctgagactc 60 tcctgtgcag cctctggatt cacctttagc aactatggca tgacctgggt ccgccaggct 120
ccagggaagg gcctggaatg ggtctcagct attactggtg gtggtggtag cacatactac 180
tcaaactccg tgaagggccg gttcaccatc tccagagaca attccaagaa cacggtgtat 240
ctgcgaatga acagtgtgag agccgaggac acggccgtat attactgtgc gaaatataag 300
tggaacttcg tggacgactg gggccaggga accacggtca ccgtctcctc a 351

<210> SEQ ID NO 66
<211> LENGTH: 117
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Thr Trp Val Arg Gln Ala Pro Gly Lys Gly Leu Glu Trp Val
35 40 45

-continued

```
Ser Ala Ile Thr Gly Gly Gly Gly Ser Thr Tyr Tyr Ser Asn Ser Val
    50                  55                  60

Lys Gly Arg Phe Thr Ile Ser Arg Asp Asn Ser Lys Asn Thr Val Tyr
65                  70                  75                  80

Leu Arg Met Asn Ser Val Arg Ala Glu Asp Thr Ala Val Tyr Tyr Cys
                85                  90                  95

Ala Lys Tyr Lys Trp Asn Phe Val Asp Asp Trp Gly Gln Gly Thr Thr
            100                 105                 110

Val Thr Val Ser Ser
        115


<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

ggattcacct ttagcaacta tggc                                            24


<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Asn Tyr Gly
1               5


<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69

attactggtg gtggtggtag caca                                            24


<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Thr Gly Gly Gly Gly Ser Thr
1               5


<210> SEQ ID NO 71
<211> LENGTH: 30
<212> TYPE: DNA
<213> ORGANISM: Artificial Sequence
<220> FEATURE:
<223> OTHER INFORMATION: synthetic

<400> SEQUENCE: 71

gcgaaatata agtggaactt cgtggacgac                                      30
```

<210> SEQ ID NO 72
<211> LENGTH: 10
<212> TYPE: PRT
<213> ORGANISM: Artificial Sequence
<220> FEATURE:
<223> OTHER INFORMATION: synthetic

<400> SEQUENCE: 72

Ala Lys Tyr Lys Trp Asn Phe Val Asp Asp
1               5                   10

<210> SEQ ID NO 73
<211> LENGTH: 360
<212> TYPE: DNA
<213> ORGANISM: Artificial Sequence
<220> FEATURE:
<223> OTHER INFORMATION: synthetic

<400> SEQUENCE: 73
gaggtgcagc tggtggagtc tgggggaggc ttggtacagc ctggggggtc cctgagactc      60
tcctgtgttg cctctggatt caccttcaat aaatacgaca tgcactgggt ccgccaaact     120
actggaaaag gtctagagtg ggtctcaggt attgatactg atggtgacac atactatcca     180
ggctccgtga agggccgatt caccatctcc agagaaaatg ccgagaactc cctgtatctt     240
caaatgaacg gcctgagagt cggggacacg gctgtgtatt actgtgcaag atggccttgg     300
agtggtttct atggtgcttt tgatatctgg ggccaaggga caatggtcac cgtctcttca     360

<210> SEQ ID NO 74
<211> LENGTH: 120
<212> TYPE: PRT
<213> ORGANISM: Artificial Sequence
<220> FEATURE:
<223> OTHER INFORMATION: synthetic

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Asn Lys Tyr
            20                  25                  30

Asp Met His Trp Val Arg Gln Thr Thr Gly Lys Gly Leu Glu Trp Val
        35                  40                  45

Ser Gly Ile Asp Thr Asp Gly Asp Thr Tyr Tyr Pro Gly Ser Val Lys
    50                  55                  60

Gly Arg Phe Thr Ile Ser Arg Glu Asn Ala Glu Asn Ser Leu Tyr Leu
65                  70                  75                  80

Gln Met Asn Gly Leu Arg Val Gly Asp Thr Ala Val Tyr Tyr Cys Ala
                85                  90                  95

Arg Trp Pro Trp Ser Gly Phe Tyr Gly Ala Phe Asp Ile Trp Gly Gln
            100                 105                 110

Gly Thr Met Val Thr Val Ser Ser
        115                 120

<210> SEQ ID NO 75
<211> LENGTH: 24
<212> TYPE: DNA
<213> ORGANISM: Artificial Sequence
<220> FEATURE:
<223> OTHER INFORMATION: synthetic

<400> SEQUENCE: 75
ggattcacct tcaataaata cgac                                             24

-continued

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Phe Thr Phe Asn Lys Tyr Asp
1               5

<210> SEQ ID NO 77
<211> LENGTH: 21
<212> TYPE: DNA
<213> ORGANISM: Artificial Sequence
<220> FEATURE:
<223> OTHER INFORMATION: synthetic

<400> SEQUENCE: 77
attgatactg atggtgacac a 21

<210> SEQ ID NO 78
<211> LENGTH: 7
<212> TYPE: PRT
<213> ORGANISM: Artificial Sequence
<220> FEATURE:
<223> OTHER INFORMATION: synthetic

<400> SEQUENCE: 78

Ile Asp Thr Asp Gly Asp Thr
1               5

<210> SEQ ID NO 79
<211> LENGTH: 42
<212> TYPE: DNA
<213> ORGANISM: Artificial Sequence
<220> FEATURE:
<223> OTHER INFORMATION: synthetic

<400> SEQUENCE: 79
gcaagatggc cttggagtgg tttctatggt gcttttgata tc 42

<210> SEQ ID NO 80
<211> LENGTH: 14
<212> TYPE: PRT
<213> ORGANISM: Artificial Sequence
<220> FEATURE:
<223> OTHER INFORMATION: synthetic

<400> SEQUENCE: 80

Ala Arg Trp Pro Trp Ser Gly Phe Tyr Gly Ala Phe Asp Ile
1               5                   10

<210> SEQ ID NO 81
<211> LENGTH: 366
<212> TYPE: DNA
<213> ORGANISM: Artificial Sequence
<220> FEATURE:
<223> OTHER INFORMATION: synthetic

<400> SEQUENCE: 81
caggtgcagc tgcaggagtc gggcccagga ctggtgaagc cttcacagac cctgtccctc 60
acctgcactg tctctggtgg ctccatcagc agtggtaatt actactggaa ctggatccgc 120
caacagccag gagagggcct ggagtggatt gcttacatct atcacaatgg ggtcaccaac 180
ttcaatccgt ccctcaagag tcgacttact atatcagtag acacgtctaa gactcagttc 240

-continued tccctgaagt tgaggtctgt gactgccgcg gacacggccg tttattactg tgcgagatca 300
ggcagctggt tcgagaactg gtacttcgat ctctggggcc gtggcaccct ggtcactgtc 360
tcctca 366

<210> SEQ ID NO 82
<211> LENGTH: 122
<212> TYPE: PRT
<213> ORGANISM: Artificial Sequence
<220> FEATURE:
<223> OTHER INFORMATION: synthetic

<400> SEQUENCE: 82

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Asn Tyr Tyr Trp Asn Trp Ile Arg Gln Gln Pro Gly Glu Gly Leu Glu
35 40 45

Trp Ile Ala Tyr Ile Tyr His Asn Gly Val Thr Asn Phe Asn Pro Ser
50 55 60

Leu Lys Ser Arg Leu Thr Ile Ser Val Asp Thr Ser Lys Thr Gln Phe
65 70 75 80

Ser Leu Lys Leu Arg Ser Val Thr Ala Ala Asp Thr Ala Val Tyr Tyr
85 90 95

Cys Ala Arg Ser Gly Ser Trp Phe Glu Asn Trp Tyr Phe Asp Leu Trp
100 105 110

Gly Arg Gly Thr Leu Val Thr Val Ser Ser
115 120

<210> SEQ ID NO 83
<211> LENGTH: 30
<212> TYPE: DNA
<213> ORGANISM: Artificial Sequence
<220> FEATURE:
<223> OTHER INFORMATION: synthetic

<400> SEQUENCE: 83
ggtggctcca tcagcagtgg taattactac 30

<210> SEQ ID NO 84
<211> LENGTH: 10
<212> TYPE: PRT
<213> ORGANISM: Artificial Sequence
<220> FEATURE:
<223> OTHER INFORMATION: synthetic

<400> SEQUENCE: 84

Gly Gly Ser Ile Ser Ser Gly Asn Tyr Tyr
1 5 10

<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85
atctatcaca atggggtcac c 21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Tyr His Asn Gly Val Thr
1               5

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87
gcgagatcag gcagctggtt cgagaactgg tacttcgatc tc 42

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Ser Gly Ser Trp Phe Glu Asn Trp Tyr Phe Asp Leu
1               5                   10

<210> SEQ ID NO 89
<211> LENGTH: 324
<212> TYPE: DNA
<213> ORGANISM: Artificial Sequence
<220> FEATURE:
<223> OTHER INFORMATION: synthetic

<400> SEQUENCE: 89
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccttg gacgttcggc 300
caagggacca aggtggaaat caaa 324

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 91
<211> LENGTH: 21
<212> TYPE: DNA
<213> ORGANISM: Artificial Sequence
<220> FEATURE:
<223> OTHER INFORMATION: synthetic

<400> SEQUENCE: 91

cagagtgtta gcagcagcta c                                               21


<210> SEQ ID NO 92
<211> LENGTH: 7
<212> TYPE: PRT
<213> ORGANISM: Artificial Sequence
<220> FEATURE:
<223> OTHER INFORMATION: synthetic

<400> SEQUENCE: 92

Gln Ser Val Ser Ser Ser Tyr
1               5


<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93

ggtgcatcc                                                              9


<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Gly Ala Ser
1


<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95

cagcagtatg gtagctcacc ttggacg                                         27


<210> SEQ ID NO 96
<211> LENGTH: 9
<212> TYPE: PRT
<213> ORGANISM: Artificial Sequence
```

<220> FEATURE:
<223> OTHER INFORMATION: synthetic

<400> SEQUENCE: 96

Gln Gln Tyr Gly Ser Ser Pro Trp Thr
1               5

<210> SEQ ID NO 97
<211> LENGTH: 360
<212> TYPE: DNA
<213> ORGANISM: Artificial Sequence
<220> FEATURE:
<223> OTHER INFORMATION: synthetic

<400> SEQUENCE: 97
caggtgcagc tgcaggagtc gggcccagga ctggtgaagc cttcggagac cctgtccctc     60
acctgcactg tctctggtgg ctccatcagt aattcctact ggagctggat ccggcagccc    120
ccagggaagg gactggagtg gattggatat gtctattccc gtgggaacac caagtacaac    180
ccctccctca cgagtcgagt caccatgtca tttgacacgt ccaagaacca gttctccctg    240
aaactgaggt ctgtgaccgc cgcagacacg gccgtgtatt actgtgcgag aagcagcagc    300
tggtacgagg actggtactt cgatctctgg ggccgtggca ccctggtcac tgtctcctca    360

<210> SEQ ID NO 98
<211> LENGTH: 120
<212> TYPE: PRT
<213> ORGANISM: Artificial Sequence
<220> FEATURE:
<223> OTHER INFORMATION: synthetic

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Tyr Trp Ser Trp Ile Arg Gln Pro Pro Gly Lys Gly Leu Glu Trp Ile
        35                  40                  45

Gly Tyr Val Tyr Ser Arg Gly Asn Thr Lys Tyr Asn Pro Ser Leu Thr
    50                  55                  60

Ser Arg Val Thr Met Ser Phe Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Ser Ser Ser Trp Tyr Glu Asp Trp Tyr Phe Asp Leu Trp Gly Arg
            100                 105                 110

Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggtggctcca tcagtaattc ctac                                            24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Gly Ser Ile Ser Asn Ser Tyr
1               5

<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
gtctattccc gtgggaacac c                                            21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

Val Tyr Ser Arg Gly Asn Thr
1               5

<210> SEQ ID NO 103
<211> LENGTH: 42
<212> TYPE: DNA
<213> ORGANISM: Artificial Sequence
<220> FEATURE:
<223> OTHER INFORMATION: synthetic

<400> SEQUENCE: 103
gcgagaagca gcagctggta cgaggactgg tacttcgatc tc                      42

<210> SEQ ID NO 104
<211> LENGTH: 14
<212> TYPE: PRT
<213> ORGANISM: Artificial Sequence
<220> FEATURE:
<223> OTHER INFORMATION: synthetic

<400> SEQUENCE: 104

Ala Arg Ser Ser Ser Trp Tyr Glu Asp Trp Tyr Phe Asp Leu
1               5                   10

<210> SEQ ID NO 105
<211> LENGTH: 354
<212> TYPE: DNA
<213> ORGANISM: Artificial Sequence
<220> FEATURE:
<223> OTHER INFORMATION: synthetic

<400> SEQUENCE: 105
caggtgcagc tacagcagtg gggcgcaggg ctgtttaagc cttcggagac cctgtccctc    60
acctgcgatg tctatggtgg gtccttcaga ggttattatt ggagttggat ccgccagccc   120
ccagggaagg ggctggagtg gattggggaa atcagttata gtggtttcac caattacaac   180
ccgtccctca agagtcgagt catcatatca atagatacgt ccaagaacca gttctccctg   240

-continued

```
aagatgagct ctgtgaccgc cgcggacacg gctgtttatt actgtgcgag agttacctat    300

ggttatggga cctttgatta ttggggccag ggaaccctgg tcaccgtctc ctca          354


<210> SEQ ID NO 106
<211> LENGTH: 118
<212> TYPE: PRT
<213> ORGANISM: Artificial Sequence
<220> FEATURE:
<223> OTHER INFORMATION: synthetic

<400> SEQUENCE: 106

Gln Val Gln Leu Gln Gln Trp Gly Ala Gly Leu Phe Lys Pro Ser Glu
1               5                   10                  15

Thr Leu Ser Leu Thr Cys Asp Val Tyr Gly Gly Ser Phe Arg Gly Tyr
            20                  25                  30

Tyr Trp Ser Trp Ile Arg Gln Pro Pro Gly Lys Gly Leu Glu Trp Ile
        35                  40                  45

Gly Glu Ile Ser Tyr Ser Gly Phe Thr Asn Tyr Asn Pro Ser Leu Lys
    50                  55                  60

Ser Arg Val Ile Ile Ser Ile Asp Thr Ser Lys Asn Gln Phe Ser Leu
65                  70                  75                  80

Lys Met Ser Ser Val Thr Ala Ala Asp Thr Ala Val Tyr Tyr Cys Ala
                85                  90                  95

Arg Val Thr Tyr Gly Tyr Gly Thr Phe Asp Tyr Trp Gly Gln Gly Thr
            100                 105                 110

Leu Val Thr Val Ser Ser
        115


<210> SEQ ID NO 107
<211> LENGTH: 24
<212> TYPE: DNA
<213> ORGANISM: Artificial Sequence
<220> FEATURE:
<223> OTHER INFORMATION: synthetic

<400> SEQUENCE: 107

ggtgggtcct tcagaggtta ttat                                            24


<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108

Gly Gly Ser Phe Arg Gly Tyr Tyr
1               5


<210> SEQ ID NO 109
<211> LENGTH: 21
<212> TYPE: DNA
<213> ORGANISM: Artificial Sequence
<220> FEATURE:
<223> OTHER INFORMATION: synthetic

<400> SEQUENCE: 109

atcagttata gtggtttcac c                                               21
```

<210> SEQ ID NO 110
<211> LENGTH: 7
<212> TYPE: PRT
<213> ORGANISM: Artificial Sequence
<220> FEATURE:
<223> OTHER INFORMATION: synthetic

<400> SEQUENCE: 110

Ile Ser Tyr Ser Gly Phe Thr
1               5

<210> SEQ ID NO 111
<211> LENGTH: 36
<212> TYPE: DNA
<213> ORGANISM: Artificial Sequence
<220> FEATURE:
<223> OTHER INFORMATION: synthetic

<400> SEQUENCE: 111
gcgagagtta cctatggtta tgggaccttt gattat 36

<210> SEQ ID NO 112
<211> LENGTH: 12
<212> TYPE: PRT
<213> ORGANISM: Artificial Sequence
<220> FEATURE:
<223> OTHER INFORMATION: synthetic

<400> SEQUENCE: 112

Ala Arg Val Thr Tyr Gly Tyr Gly Thr Phe Asp Tyr
1               5                   10

<210> SEQ ID NO 113
<211> LENGTH: 1165
<212> TYPE: PRT
<213> ORGANISM: Artificial Sequence
<220> FEATURE:
<223> OTHER INFORMATION: hLEPR Accession No P48357

<400> SEQUENCE: 113

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

-continued

```
Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590
```

-continued

```
Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925

Lys Asn Lys Asp Glu Met Met Pro Thr Thr Val Val Ser Leu Leu Ser
    930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu  Glu Gln Gly Leu Ile  Asn Ser Ser
        995                 1000                 1005
```

-continued

Val Thr Lys Cys Phe Ser Ser Lys Asn Ser Pro Leu Lys Asp Ser
    1010                1015                1020

Phe Ser Asn Ser Ser Trp Glu Ile Glu Ala Gln Ala Phe Phe Ile
    1025                1030                1035

Leu Ser Asp Gln His Pro Asn Ile Ile Ser Pro His Leu Thr Phe
    1040                1045                1050

Ser Glu Gly Leu Asp Glu Leu Leu Lys Leu Glu Gly Asn Phe Pro
    1055                1060                1065

Glu Glu Asn Asn Asp Lys Lys Ser Ile Tyr Tyr Leu Gly Val Thr
    1070                1075                1080

Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 114
<211> LENGTH: 846
<212> TYPE: PRT
<213> ORGANISM: Artificial Sequence
<220> FEATURE:
<223> OTHER INFORMATION: hLEPR.mmh aa 1-818: F22-D839 of P48357 aa
      819-846: myc-myc-hexahistidine tag

<400> SEQUENCE: 114

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

-continued

```
Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605
```

-continued

Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
                805                 810                 815

Ser Asp Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845

<210> SEQ ID NO 115
<211> LENGTH: 1051
<212> TYPE: PRT
<213> ORGANISM: Artificial Sequence
<220> FEATURE:
<223> OTHER INFORMATION: hLEPR.mFc aa 1-818: F22-D839 of P48357 aa
      819-1051: mouse IgG2a (E98-K330 of P01863)

<400> SEQUENCE: 115

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

-continued

```
Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540
```

-continued

```
Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
                805                 810                 815

Ser Asp Glu Pro Arg Gly Pro Thr Ile Lys Pro Cys Pro Pro Cys Lys
            820                 825                 830

Cys Pro Ala Pro Asn Leu Leu Gly Gly Pro Ser Val Phe Ile Phe Pro
        835                 840                 845

Pro Lys Ile Lys Asp Val Leu Met Ile Ser Leu Ser Pro Ile Val Thr
    850                 855                 860

Cys Val Val Val Asp Val Ser Glu Asp Asp Pro Asp Val Gln Ile Ser
865                 870                 875                 880

Trp Phe Val Asn Asn Val Glu Val His Thr Ala Gln Thr Gln Thr His
                885                 890                 895

Arg Glu Asp Tyr Asn Ser Thr Leu Arg Val Val Ser Ala Leu Pro Ile
            900                 905                 910

Gln His Gln Asp Trp Met Ser Gly Lys Glu Phe Lys Cys Lys Val Asn
        915                 920                 925

Asn Lys Asp Leu Pro Ala Pro Ile Glu Arg Thr Ile Ser Lys Pro Lys
    930                 935                 940

Gly Ser Val Arg Ala Pro Gln Val Tyr Val Leu Pro Pro Pro Glu Glu
945                 950                 955                 960
```

-continued

```
Glu Met Thr Lys Lys Gln Val Thr Leu Thr Cys Met Val Thr Asp Phe
                965                 970                 975

Met Pro Glu Asp Ile Tyr Val Glu Trp Thr Asn Asn Gly Lys Thr Glu
            980                 985                 990

Leu Asn Tyr Lys Asn Thr Glu Pro  Val Leu Asp Ser Asp  Gly Ser Tyr
        995                 1000                 1005

Phe Met  Tyr Ser Lys Leu Arg  Val Glu Lys Lys Asn  Trp Val Glu
    1010                 1015                 1020

Arg Asn  Ser Tyr Ser Cys Ser  Val Val His Glu Gly  Leu His Asn
    1025                 1030                 1035

His His  Thr Thr Lys Ser Phe  Ser Arg Thr Pro Gly  Lys
    1040                 1045                 1050
```

<210> SEQ ID NO 116
<211> LENGTH: 1045
<212> TYPE: PRT
<213> ORGANISM: Artificial Sequence
<220> FEATURE:
<223> OTHER INFORMATION: hLEPR.hFc aa 1-818: F22-D839 of P48357 aa 819-1045: human IgG1 tag (D104-K330 of P01857)

<400> SEQUENCE: 116

```
Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270
```

-continued

```
Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685
```

-continued

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
                805                 810                 815

Ser Asp Asp Lys Thr His Thr Cys Pro Pro Cys Pro Ala Pro Glu Leu
            820                 825                 830

Leu Gly Gly Pro Ser Val Phe Leu Phe Pro Pro Lys Pro Lys Asp Thr
        835                 840                 845

Leu Met Ile Ser Arg Thr Pro Glu Val Thr Cys Val Val Val Asp Val
    850                 855                 860

Ser His Glu Asp Pro Glu Val Lys Phe Asn Trp Tyr Val Asp Gly Val
865                 870                 875                 880

Glu Val His Asn Ala Lys Thr Lys Pro Arg Glu Glu Gln Tyr Asn Ser
                885                 890                 895

Thr Tyr Arg Val Val Ser Val Leu Thr Val Leu His Gln Asp Trp Leu
            900                 905                 910

Asn Gly Lys Glu Tyr Lys Cys Lys Val Ser Asn Lys Ala Leu Pro Ala
        915                 920                 925

Pro Ile Glu Lys Thr Ile Ser Lys Ala Lys Gly Gln Pro Arg Glu Pro
    930                 935                 940

Gln Val Tyr Thr Leu Pro Pro Ser Arg Asp Glu Leu Thr Lys Asn Gln
945                 950                 955                 960

Val Ser Leu Thr Cys Leu Val Lys Gly Phe Tyr Pro Ser Asp Ile Ala
                965                 970                 975

Val Glu Trp Glu Ser Asn Gly Gln Pro Glu Asn Asn Tyr Lys Thr Thr
            980                 985                 990

Pro Pro Val Leu Asp Ser Asp Gly  Ser Phe Phe Leu Tyr  Ser Lys Leu
        995                 1000                1005

Thr Val  Asp Lys Ser Arg Trp  Gln Gln Gly Asn Val  Phe Ser Cys
    1010                1015                1020

Ser Val  Met His Glu Ala Leu  His Asn His Tyr Thr  Gln Lys Ser
    1025                1030                1035

Leu Ser  Leu Ser Pro Gly Lys
    1040                1045

<210> SEQ ID NO 117
<211> LENGTH: 844
<212> TYPE: PRT
<213> ORGANISM: Artificial Sequence
<220> FEATURE:
<223> OTHER INFORMATION: MfLEPR.mmh aa 1-816: Macaca fascicularis
      F22-D837 with a T827A substitution from XP_005543194.1 aa 817-844:
      myc-myc-hexahistidine tag

<400> SEQUENCE: 117

```
Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Leu Asn Gly His Tyr Glu Thr Ala Val Glu
        35                  40                  45

Phe Asn Ser Ser Asp Thr His Phe Ser Asn Leu Ser Lys Thr Thr Phe
    50                  55                  60

His Cys Cys Phe Arg Ser Glu Gln Asp Arg Asn Cys Ser Leu Cys Ala
65                  70                  75                  80

Asp Asn Ile Glu Gly Lys Thr Phe Val Ser Thr Val Asn Ser Ser Val
                85                  90                  95

Phe Gln Gln Met Gly Ala Asn Trp Asn Ile Gln Cys Trp Leu Lys Gly
            100                 105                 110

Asp Leu Lys Leu Phe Ile Cys Tyr Val Glu Ser Leu Phe Lys Asn Pro
        115                 120                 125

Phe Lys Asn Tyr Lys His Lys Val His Leu Leu Tyr Val Leu Pro Glu
    130                 135                 140

Val Leu Glu Asp Ser Pro Leu Val Pro Gln Lys Gly Ser Phe Gln Met
145                 150                 155                 160

Val His Cys Asn Cys Ser Val His Glu Arg Cys Glu Cys Leu Val Pro
                165                 170                 175

Val Pro Thr Ala Lys Leu Asn Asp Thr Leu Leu Met Cys Leu Lys Ile
            180                 185                 190

Thr Ser Gly Gly Val Ile Phe Gln Ser Pro Leu Met Ser Val Gln Pro
        195                 200                 205

Ile Asn Met Val Lys Pro Asp Pro Pro Leu Gly Leu Arg Met Glu Ile
    210                 215                 220

Thr Asp Asp Gly Asn Leu Lys Ile Ser Trp Ser Ser Pro Pro Leu Val
225                 230                 235                 240

Pro Phe Pro Leu Gln Tyr Glu Val Lys Tyr Ser Glu Asn Ser Thr Thr
                245                 250                 255

Val Ile Arg Glu Ala Asp Lys Ile Val Ser Ala Thr Ser Leu Leu Val
            260                 265                 270

Asp Gly Ile Leu Pro Gly Ser Ser Tyr Glu Val Gln Val Arg Gly Lys
        275                 280                 285

Arg Leu Asp Gly Pro Gly Ile Trp Ser Asp Trp Ser Thr Pro His Val
    290                 295                 300

Phe Thr Thr Gln Asp Val Ile Tyr Phe Pro Pro Lys Ile Leu Thr Ser
305                 310                 315                 320

Val Gly Ser Asn Val Ser Phe His Cys Ile Tyr Lys Asn Glu Asn Lys
                325                 330                 335

Ile Val Ser Ser Lys Lys Ile Val Trp Trp Met Asn Leu Ala Glu Lys
            340                 345                 350

Ile Pro Gln Ser Gln Tyr Asp Val Val Ser Asp His Val Ser Lys Val
        355                 360                 365

Thr Phe Phe Asn Leu Asn Glu Thr Lys Pro Arg Gly Lys Phe Thr Tyr
    370                 375                 380

Asp Ala Val Tyr Cys Cys Asn Glu His Glu Cys His His Arg Tyr Ala
385                 390                 395                 400

Glu Leu Tyr Val Ile Asp Val Asn Ile Asn Ile Ser Cys Glu Thr Asp
                405                 410                 415
```

-continued

```
Gly His Leu Thr Lys Met Thr Cys Arg Trp Ser Thr Asn Thr Ile Gln
            420                 425                 430

Ser Leu Ala Gly Ser Thr Leu Gln Leu Arg Tyr Arg Arg Ser Ser Leu
        435                 440                 445

Tyr Cys Phe Asp Ile Pro Ser Ile His Pro Ile Ser Lys Pro Lys Asp
    450                 455                 460

Cys Tyr Leu Gln Ser Asp Gly Phe Tyr Glu Cys Val Phe Gln Pro Ile
465                 470                 475                 480

Phe Leu Leu Ser Gly Tyr Thr Met Trp Ile Arg Ile Asn His Pro Leu
                485                 490                 495

Gly Ser Leu Asp Ser Pro Pro Thr Cys Val Leu Pro Asp Ser Val Val
            500                 505                 510

Lys Pro Leu Pro Pro Ser Ser Val Lys Ala Glu Ile Ile Lys Asn Ile
        515                 520                 525

Gly Leu Leu Lys Ile Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Met Tyr Asp Val Tyr Asp Ala Lys Ser Lys Ser Val Ser Leu Pro
                565                 570                 575

Val Pro Asp Phe Cys Ala Val Tyr Ala Val Gln Val Arg Cys Lys Arg
            580                 585                 590

Ser Asp Gly Leu Gly Leu Trp Ser Asn Trp Ser Asn Pro Ala Tyr Thr
        595                 600                 605

Val Val Met Asp Ile Lys Val Pro Met Arg Gly Pro Glu Phe Trp Arg
    610                 615                 620

Ile Ile Asn Gly Asp Thr Met Lys Lys Glu Lys Asn Val Thr Leu Leu
625                 630                 635                 640

Trp Lys Pro Leu Met Lys Asn Asp Ser Leu Cys Ser Val Gln Arg Tyr
                645                 650                 655

Val Ile Asn His His Thr Ser Cys Asn Gly Thr Trp Ser Glu Asp Val
            660                 665                 670

Gly Asn His Thr Lys Phe Thr Phe Leu Trp Thr Glu Gln Ala His Thr
        675                 680                 685

Val Thr Val Leu Ala Ile Asn Ser Ile Gly Ala Ser Val Ala Asn Phe
    690                 695                 700

Asn Leu Thr Phe Ser Trp Pro Met Ser Lys Val Asn Ile Val Gln Ser
705                 710                 715                 720

Leu Ser Ala Tyr Pro Leu Asn Ser Ser Cys Val Ile Leu Ser Trp Ile
                725                 730                 735

Leu Ser Pro Ser Asp Tyr Lys Leu Met Tyr Phe Ile Ile Glu Trp Lys
            740                 745                 750

Asn Leu Asn Glu Asp Gly Glu Ile Lys Trp Leu Arg Ile Ser Ser Ser
        755                 760                 765

Val Lys Lys Tyr Tyr Ile His Asp His Phe Ile Pro Ile Glu Lys Tyr
    770                 775                 780

Gln Phe Ser Leu Tyr Pro Ile Phe Met Glu Gly Val Gly Lys Pro Lys
785                 790                 795                 800

Ile Ile Asn Ser Phe Ala Gln Asp Asn Thr Glu Lys His Gln Asn Asp
                805                 810                 815

Glu Gln Lys Leu Ile Ser Glu Glu Asp Leu Gly Gly Glu Gln Lys Leu
            820                 825                 830

Ile Ser Glu Glu Asp Leu His His His His His His
        835                 840
```

<210> SEQ ID NO 118
<211> LENGTH: 846
<212> TYPE: PRT
<213> ORGANISM: Artificial Sequence
<220> FEATURE:
<223> OTHER INFORMATION: mLEPR.mmh aa 1-818: Mouse LEPR (L22-G839 of NP_666258.2) aa 817-846: myc-myc-hexahistidine tag

<400> SEQUENCE: 118

```
Leu Asn Leu Ala Tyr Pro Ile Ser Pro Trp Lys Phe Lys Leu Phe Cys
1               5                   10                  15

Gly Pro Pro Asn Thr Thr Asp Asp Ser Phe Leu Ser Pro Ala Gly Ala
            20                  25                  30

Pro Asn Asn Ala Ser Ala Leu Lys Gly Ala Ser Glu Ala Ile Val Glu
        35                  40                  45

Ala Lys Phe Asn Ser Ser Gly Ile Tyr Val Pro Glu Leu Ser Lys Thr
    50                  55                  60

Val Phe His Cys Cys Phe Gly Asn Glu Gln Gly Gln Asn Cys Ser Ala
65                  70                  75                  80

Leu Thr Asp Asn Thr Glu Gly Lys Thr Leu Ala Ser Val Val Lys Ala
                85                  90                  95

Ser Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Pro Lys
        115                 120                 125

Asn Pro Phe Lys Asn Tyr Asp Ser Lys Val His Leu Leu Tyr Asp Leu
    130                 135                 140

Pro Glu Val Ile Asp Asp Ser Pro Leu Pro Pro Leu Lys Asp Ser Phe
145                 150                 155                 160

Gln Thr Val Gln Cys Asn Cys Ser Leu Arg Gly Cys Glu Cys His Val
                165                 170                 175

Pro Val Pro Arg Ala Lys Leu Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu His Met Glu
    210                 215                 220

Val Thr Asp Asp Gly Asn Leu Lys Ile Ser Trp Asp Ser Gln Thr Met
225                 230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Ala Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Ser Pro Gln Val
    290                 295                 300

Phe Thr Thr Gln Asp Val Val Tyr Phe Pro Pro Lys Ile Leu Thr Ser
305                 310                 315                 320

Val Gly Ser Asn Ala Ser Phe His Cys Ile Tyr Lys Asn Glu Asn Gln
                325                 330                 335

Ile Ile Ser Ser Lys Gln Ile Val Trp Trp Arg Asn Leu Ala Glu Lys
            340                 345                 350

Ile Pro Glu Ile Gln Tyr Ser Ile Val Ser Asp Arg Val Ser Lys Val
        355                 360                 365
```

-continued

```
Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Ser Pro Ser Ile His Pro Thr Ser Glu Pro Lys Asn
    450                 455                 460

Cys Val Leu Gln Arg Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Val Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Thr His Glu Val Phe Asp Ala Lys Ser Lys Ser Ala Ser Leu Leu
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Lys Met Asp Gly Asp Val Thr Lys Lys Glu Arg Asn Val Thr Leu Leu
625                 630                 635                 640

Trp Lys Pro Leu Thr Lys Asn Asp Ser Leu Cys Ser Val Arg Arg Tyr
                645                 650                 655

Val Val Lys His Arg Thr Ala His Asn Gly Thr Trp Ser Glu Asp Val
            660                 665                 670

Gly Asn Arg Thr Asn Leu Thr Phe Leu Trp Thr Glu Pro Ala His Thr
        675                 680                 685

Val Thr Val Leu Ala Val Asn Ser Leu Gly Ala Ser Leu Val Asn Phe
    690                 695                 700

Asn Leu Thr Phe Ser Trp Pro Met Ser Lys Val Ser Ala Val Glu Ser
705                 710                 715                 720

Leu Ser Ala Tyr Pro Leu Ser Ser Ser Cys Val Ile Leu Ser Trp Thr
                725                 730                 735

Leu Ser Pro Asp Asp Tyr Ser Leu Leu Tyr Leu Val Ile Glu Trp Lys
            740                 745                 750

Ile Leu Asn Glu Asp Asp Gly Met Lys Trp Leu Arg Ile Pro Ser Asn
        755                 760                 765

Val Lys Lys Phe Tyr Ile His Asp Asn Phe Ile Pro Ile Glu Lys Tyr
    770                 775                 780
```

-continued

```
Gln Phe Ser Leu Tyr Pro Val Phe Met Glu Gly Val Gly Lys Pro Lys
785                 790                 795                 800

Ile Ile Asn Gly Phe Thr Lys Asp Ala Ile Asp Lys Gln Gln Asn Asp
                805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845


<210> SEQ ID NO 119
<211> LENGTH: 846
<212> TYPE: PRT
<213> ORGANISM: Artificial Sequence
<220> FEATURE:
<223> OTHER INFORMATION: rLEPR.mmh aa 1-818: Rat LEPR (L22-G839 of
      NP_036728.1) aa 819-846: myc-myc-hexahistidine tag

<400> SEQUENCE: 119

Leu Asn Leu Ala Tyr Pro Thr Ser Pro Trp Arg Phe Lys Leu Phe Cys
1               5                   10                  15

Ala Pro Pro Ser Thr Thr Asp Asp Ser Phe Leu Ser Pro Ala Gly Val
            20                  25                  30

Pro Asn Asn Thr Ser Ser Leu Lys Gly Ala Ser Glu Ala Leu Val Glu
        35                  40                  45

Ala Lys Phe Asn Ser Thr Gly Ile Tyr Val Ser Glu Leu Ser Lys Thr
    50                  55                  60

Ile Phe His Cys Cys Phe Gly Asn Glu Gln Gly Gln Asn Cys Ser Ala
65                  70                  75                  80

Leu Thr Gly Asn Thr Glu Gly Lys Thr Leu Ala Ser Val Val Lys Pro
                85                  90                  95

Leu Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Leu Lys
        115                 120                 125

Asn Pro Phe Lys Asn Tyr Asp Ser Lys Val His Leu Leu Tyr Asp Leu
    130                 135                 140

Pro Glu Val Ile Asp Asp Leu Pro Leu Pro Pro Leu Lys Asp Ser Phe
145                 150                 155                 160

Gln Thr Val Gln Cys Asn Cys Ser Val Arg Glu Cys Glu Cys His Val
                165                 170                 175

Pro Val Pro Arg Ala Lys Val Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu Arg Met Glu
    210                 215                 220

Val Thr Asp Asp Gly Asn Leu Lys Ile Ser Trp Asp Ser Gln Thr Lys
225                 230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Asp Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Leu Pro Gln Leu
    290                 295                 300
```

-continued

```
Phe Thr Thr Gln Asp Val Met Tyr Phe Pro Pro Lys Ile Leu Thr Ser
305                 310                 315                 320

Val Gly Ser Asn Ala Ser Phe Cys Cys Ile Tyr Lys Asn Glu Asn Gln
                325                 330                 335

Thr Ile Ser Ser Lys Gln Ile Val Trp Trp Met Asn Leu Ala Glu Lys
            340                 345                 350

Ile Pro Glu Thr Gln Tyr Asn Thr Val Ser Asp His Ile Ser Lys Val
        355                 360                 365

Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Asn Pro Ser Ile Arg Pro Thr Ser Glu Leu Lys Asn
    450                 455                 460

Cys Val Leu Gln Thr Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Ile Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Asn Gly Lys Glu Ile Gln Trp
545                 550                 555                 560

Lys Thr His Glu Val Phe Asp Ala Lys Ser Lys Ser Ala Ser Leu Pro
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Ile Met Asp Gly Asp Ile Thr Lys Lys Glu Arg Asn Val Thr Leu Leu
625                 630                 635                 640

Trp Lys Pro Leu Met Lys Asn Asp Ser Leu Cys Ser Val Arg Arg Tyr
                645                 650                 655

Val Val Lys His Arg Thr Ala His Asn Gly Thr Trp Ser Gln Asp Val
            660                 665                 670

Gly Asn Gln Thr Asn Leu Thr Phe Leu Trp Ala Glu Ser Ala His Thr
        675                 680                 685

Val Thr Val Leu Ala Ile Asn Ser Ile Gly Ala Ser Leu Val Asn Phe
    690                 695                 700

Asn Leu Thr Phe Ser Trp Pro Met Ser Lys Val Asn Ala Val Gln Ser
705                 710                 715                 720
```

```
Leu Ser Ala Tyr Pro Leu Ser Ser Ser Cys Val Ile Leu Ser Trp Thr
                725                 730                 735

Leu Ser Pro Asn Asp Tyr Ser Leu Leu Tyr Leu Val Ile Glu Trp Lys
            740                 745                 750

Asn Leu Asn Asp Asp Asp Gly Met Lys Trp Leu Arg Ile Pro Ser Asn
        755                 760                 765

Val Asn Lys Tyr Tyr Ile His Asp Asn Phe Ile Pro Ile Glu Lys Tyr
    770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Asp Ile Ala Lys Gln Gln Asn Asp
                805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845


<210> SEQ ID NO 120
<211> LENGTH: 1045
<212> TYPE: PRT
<213> ORGANISM: Artificial Sequence
<220> FEATURE:
<223> OTHER INFORMATION: mLEPR.hFc aa 1-818: Mouse LEPR (L22-G839 of
      NP_666258.2) aa 819-1045: human IgG1 tag (D104-K330 of P01857)

<400> SEQUENCE: 120

Leu Asn Leu Ala Tyr Pro Ile Ser Pro Trp Lys Phe Lys Leu Phe Cys
1               5                   10                  15

Gly Pro Pro Asn Thr Thr Asp Asp Ser Phe Leu Ser Pro Ala Gly Ala
            20                  25                  30

Pro Asn Asn Ala Ser Ala Leu Lys Gly Ala Ser Glu Ala Ile Val Glu
        35                  40                  45

Ala Lys Phe Asn Ser Ser Gly Ile Tyr Val Pro Glu Leu Ser Lys Thr
    50                  55                  60

Val Phe His Cys Cys Phe Gly Asn Glu Gln Gly Gln Asn Cys Ser Ala
65                  70                  75                  80

Leu Thr Asp Asn Thr Glu Gly Lys Thr Leu Ala Ser Val Val Lys Ala
                85                  90                  95

Ser Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Pro Lys
        115                 120                 125

Asn Pro Phe Lys Asn Tyr Asp Ser Lys Val His Leu Leu Tyr Asp Leu
    130                 135                 140

Pro Glu Val Ile Asp Asp Ser Pro Leu Pro Pro Leu Lys Asp Ser Phe
145                 150                 155                 160

Gln Thr Val Gln Cys Asn Cys Ser Leu Arg Gly Cys Glu Cys His Val
                165                 170                 175

Pro Val Pro Arg Ala Lys Leu Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu His Met Glu
    210                 215                 220

Val Thr Asp Asp Gly Asn Leu Lys Ile Ser Trp Asp Ser Gln Thr Met
225                 230                 235                 240
```

-continued

```
Ala Pro Phe Pro Leu Gln Tyr Gln Val Lys Tyr Leu Glu Asn Ser Thr
                245                 250                 255

Ile Val Arg Glu Ala Ala Glu Ile Val Ser Ala Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Ser Pro Gln Val
    290                 295                 300

Phe Thr Thr Gln Asp Val Val Tyr Phe Pro Pro Lys Ile Leu Thr Ser
305                 310                 315                 320

Val Gly Ser Asn Ala Ser Phe His Cys Ile Tyr Lys Asn Glu Asn Gln
                325                 330                 335

Ile Ile Ser Ser Lys Gln Ile Val Trp Trp Arg Asn Leu Ala Glu Lys
            340                 345                 350

Ile Pro Glu Ile Gln Tyr Ser Ile Val Ser Asp Arg Val Ser Lys Val
        355                 360                 365

Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Ser Pro Ser Ile His Pro Thr Ser Glu Pro Lys Asn
    450                 455                 460

Cys Val Leu Gln Arg Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Val Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Thr His Glu Val Phe Asp Ala Lys Ser Lys Ser Ala Ser Leu Leu
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Lys Met Asp Gly Asp Val Thr Lys Lys Glu Arg Asn Val Thr Leu Leu
625                 630                 635                 640

Trp Lys Pro Leu Thr Lys Asn Asp Ser Leu Cys Ser Val Arg Arg Tyr
                645                 650                 655
```

-continued

```
Val Val Lys His Arg Thr Ala His Asn Gly Thr Trp Ser Glu Asp Val
            660                 665                 670

Gly Asn Arg Thr Asn Leu Thr Phe Leu Trp Thr Glu Pro Ala His Thr
        675                 680                 685

Val Thr Val Leu Ala Val Asn Ser Leu Gly Ala Ser Leu Val Asn Phe
    690                 695                 700

Asn Leu Thr Phe Ser Trp Pro Met Ser Lys Val Ser Ala Val Glu Ser
705                 710                 715                 720

Leu Ser Ala Tyr Pro Leu Ser Ser Ser Cys Val Ile Leu Ser Trp Thr
                725                 730                 735

Leu Ser Pro Asp Asp Tyr Ser Leu Leu Tyr Leu Val Ile Glu Trp Lys
            740                 745                 750

Ile Leu Asn Glu Asp Asp Gly Met Lys Trp Leu Arg Ile Pro Ser Asn
        755                 760                 765

Val Lys Lys Phe Tyr Ile His Asp Asn Phe Ile Pro Ile Glu Lys Tyr
    770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Ala Ile Asp Lys Gln Gln Asn Asp
                805                 810                 815

Ala Gly Asp Lys Thr His Thr Cys Pro Pro Cys Pro Ala Pro Glu Leu
            820                 825                 830

Leu Gly Gly Pro Ser Val Phe Leu Phe Pro Pro Lys Pro Lys Asp Thr
        835                 840                 845

Leu Met Ile Ser Arg Thr Pro Glu Val Thr Cys Val Val Val Asp Val
    850                 855                 860

Ser His Glu Asp Pro Glu Val Lys Phe Asn Trp Tyr Val Asp Gly Val
865                 870                 875                 880

Glu Val His Asn Ala Lys Thr Lys Pro Arg Glu Glu Gln Tyr Asn Ser
                885                 890                 895

Thr Tyr Arg Val Val Ser Val Leu Thr Val Leu His Gln Asp Trp Leu
            900                 905                 910

Asn Gly Lys Glu Tyr Lys Cys Lys Val Ser Asn Lys Ala Leu Pro Ala
        915                 920                 925

Pro Ile Glu Lys Thr Ile Ser Lys Ala Lys Gly Gln Pro Arg Glu Pro
    930                 935                 940

Gln Val Tyr Thr Leu Pro Pro Ser Arg Asp Glu Leu Thr Lys Asn Gln
945                 950                 955                 960

Val Ser Leu Thr Cys Leu Val Lys Gly Phe Tyr Pro Ser Asp Ile Ala
                965                 970                 975

Val Glu Trp Glu Ser Asn Gly Gln Pro Glu Asn Asn Tyr Lys Thr Thr
            980                 985                 990

Pro Pro Val Leu Asp Ser Asp Gly  Ser Phe Phe Leu Tyr  Ser Lys Leu
        995                 1000                1005

Thr Val  Asp Lys Ser Arg Trp  Gln Gln Gly Asn Val  Phe Ser Cys
    1010                1015                1020

Ser Val  Met His Glu Ala Leu  His Asn His Tyr Thr  Gln Lys Ser
    1025                1030                1035

Leu Ser  Leu Ser Pro Gly Lys
    1040                1045
```